(12) United States Patent
Strauss et al.

(10) Patent No.: US 8,771,341 B2
(45) Date of Patent: Jul. 8, 2014

(54) PROTUBERANT ANEURYSM BRIDGING DEVICE AND METHOD OF USE

(71) Applicant: Reverse Medical Corporation, Irvine, CA (US)

(72) Inventors: Brian M. Strauss, Irvine, CA (US); Jeffrey J. Valko, Irvine, CA (US); Michael R. Henson, Irvine, CA (US); Robert A. Pecor, Irvine, CA (US)

(73) Assignee: Reverse Medical Corporation, Irvine, CA (US)

( * ) Notice: Subject to any disclaimer, the term of this patent is extended or adjusted under 35 U.S.C. 154(b) by 0 days.

(21) Appl. No.: 13/647,315

(22) Filed: Oct. 8, 2012

(65) Prior Publication Data

US 2013/0116774 A1    May 9, 2013

Related U.S. Application Data

(60) Provisional application No. 61/556,122, filed on Nov. 4, 2011.

(51) Int. Cl.

| | | |
|---|---|---|
| *A61F 2/86* | (2013.01) | |
| *A61F 2/91* | (2013.01) | |
| *A61B 17/12* | (2006.01) | |
| *A61F 2/90* | (2013.01) | |
| *A61F 2/856* | (2013.01) | |
| *A61F 2/915* | (2013.01) | |
| *A61F 2/82* | (2013.01) | |
| *A61B 19/00* | (2006.01) | |

(52) U.S. Cl.
CPC ... *A61F 2/90* (2013.01); *A61F 2/91* (2013.01); *A61F 2002/91575* (2013.01); *A61B 17/12118* (2013.01); *A61F 2002/823* (2013.01); *A61F 2250/0037* (2013.01); *A61B 17/1214* (2013.01); *A61B 17/12172* (2013.01); *A61F 2/915* (2013.01); *A61B 2019/5466* (2013.01); *A61F 2/856* (2013.01)
USPC ............. 623/1.3; 623/1.11; 623/1.2; 606/200

(58) Field of Classification Search
CPC .................... A61F 2002/823; A61F 2002/821; A61F 2/90; A61F 2230/0078
USPC ............. 623/1.1, 1.11, 1.12, 1.15, 1.16, 1.18, 623/1.19, 1.2, 1.3, 1.31, 1.34, 1.35; 606/191.194, 198, 200
See application file for complete search history.

(56) References Cited

U.S. PATENT DOCUMENTS

| | | | |
|---|---|---|---|
| 6,063,111 A | 5/2000 | Hieshima et al. | |
| 6,168,616 B1 * | 1/2001 | Brown, III | .................. 623/1.11 |

(Continued)

FOREIGN PATENT DOCUMENTS

| | | |
|---|---|---|
| WO | WO0007524 A1 | 2/2000 |
| WO | WO2008151204 A1 | 12/2008 |

(Continued)

OTHER PUBLICATIONS

Combined Search and Examination Report from corresponding GB App. GB1223248.4, dated Jan. 23, 2013.

(Continued)

*Primary Examiner* — David Isabella
*Assistant Examiner* — Suba Ganesan
(74) *Attorney, Agent, or Firm* — K. David Crockett, Esq.; Crockett & Crockett, PC

(57) ABSTRACT

A bridging device for supporting occlusive masses within an aneurysm located at a vascular bifurcation.

6 Claims, 37 Drawing Sheets

(56) References Cited

U.S. PATENT DOCUMENTS

| | | | |
|---|---|---|---|
| 6,183,495 B1* | 2/2001 | Lenker et al. | 606/198 |
| 6,261,305 B1* | 7/2001 | Marotta et al. | 606/200 |
| 7,572,288 B2 | 8/2009 | Cox | |
| 8,262,720 B2 | 9/2012 | Bonsignore et al. | |
| 2003/0065384 A1 | 4/2003 | Pinchasik et al. | |
| 2003/0195616 A1 | 10/2003 | Pinchasik et al. | |
| 2004/0059407 A1* | 3/2004 | Escamilla et al. | 623/1.12 |
| 2004/0158311 A1 | 8/2004 | Berhow et al. | |
| 2005/0096728 A1* | 5/2005 | Ramer | 623/1.15 |
| 2006/0064151 A1* | 3/2006 | Guterman et al. | 623/1.3 |
| 2006/0100684 A1 | 5/2006 | Elliott | |
| 2006/0184238 A1 | 8/2006 | Kaufmann et al. | |
| 2007/0282428 A1 | 12/2007 | Igaki | |
| 2009/0228088 A1 | 9/2009 | Lowe et al. | |
| 2009/0264979 A1 | 10/2009 | Kao et al. | |
| 2009/0287297 A1 | 11/2009 | Cox | |
| 2010/0094390 A1 | 4/2010 | Goldmann et al. | |
| 2010/0152834 A1 | 6/2010 | Hannes et al. | |
| 2010/0274276 A1 | 10/2010 | Chow et al. | |
| 2011/0009941 A1 | 1/2011 | Grandfield et al. | |
| 2011/0046719 A1 | 2/2011 | Frid | |
| 2011/0166643 A1 | 7/2011 | Pulnev et al. | |
| 2012/0041540 A1 | 2/2012 | Shobayashi et al. | |
| 2012/0290067 A1* | 11/2012 | Cam et al. | 623/1.12 |
| 2013/0197624 A1 | 8/2013 | Armstrong et al. | |

FOREIGN PATENT DOCUMENTS

| | | |
|---|---|---|
| WO | WO2009017827 A1 | 2/2009 |
| WO | 2012166804 A1 | 6/2012 |
| WO | WO2012154782 A1 | 11/2012 |

OTHER PUBLICATIONS

Office Action dated Oct. 7, 2013 from U.S. Appl. No. 13/850,266.

* cited by examiner

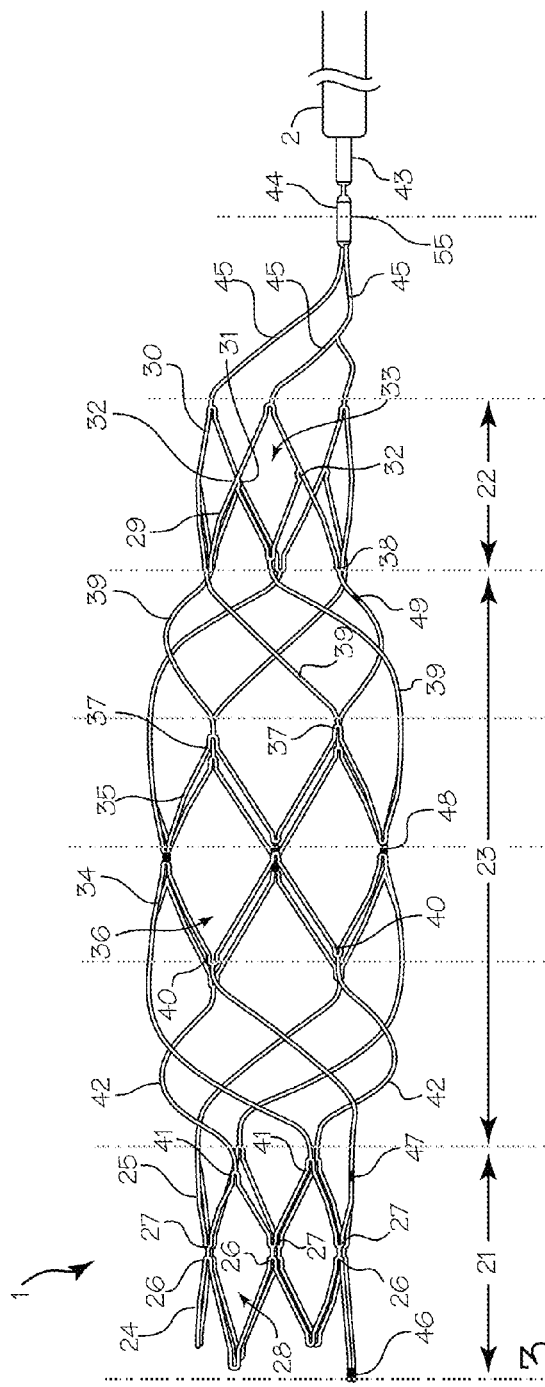
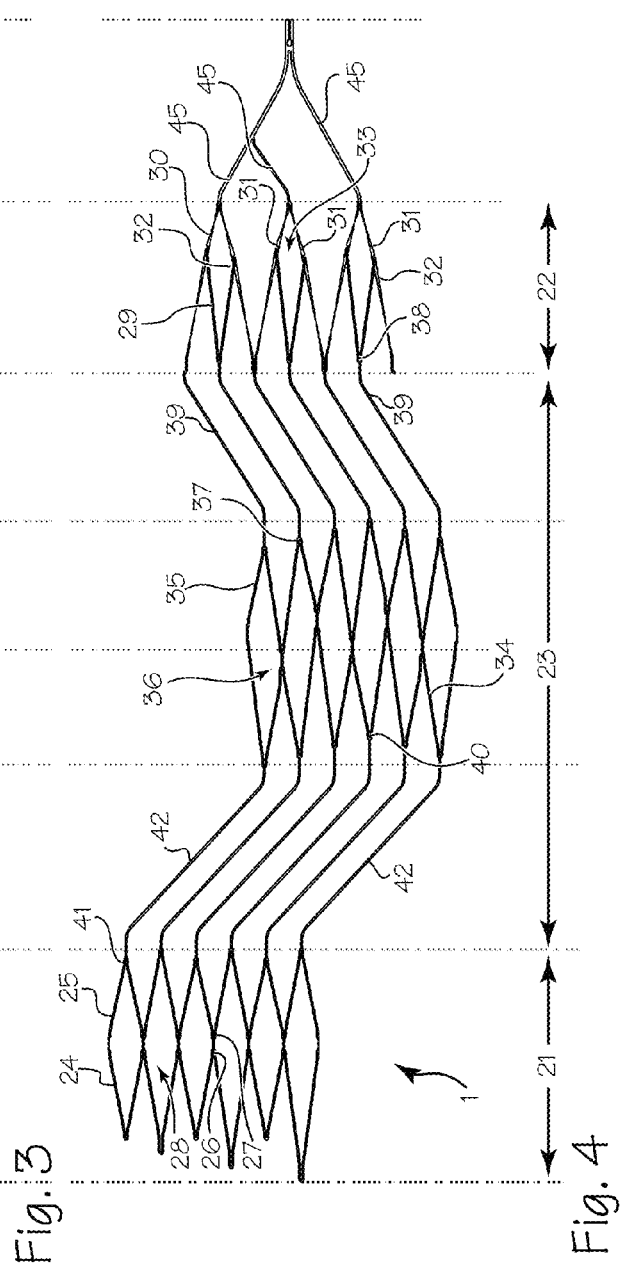
Fig. 3
Fig. 4

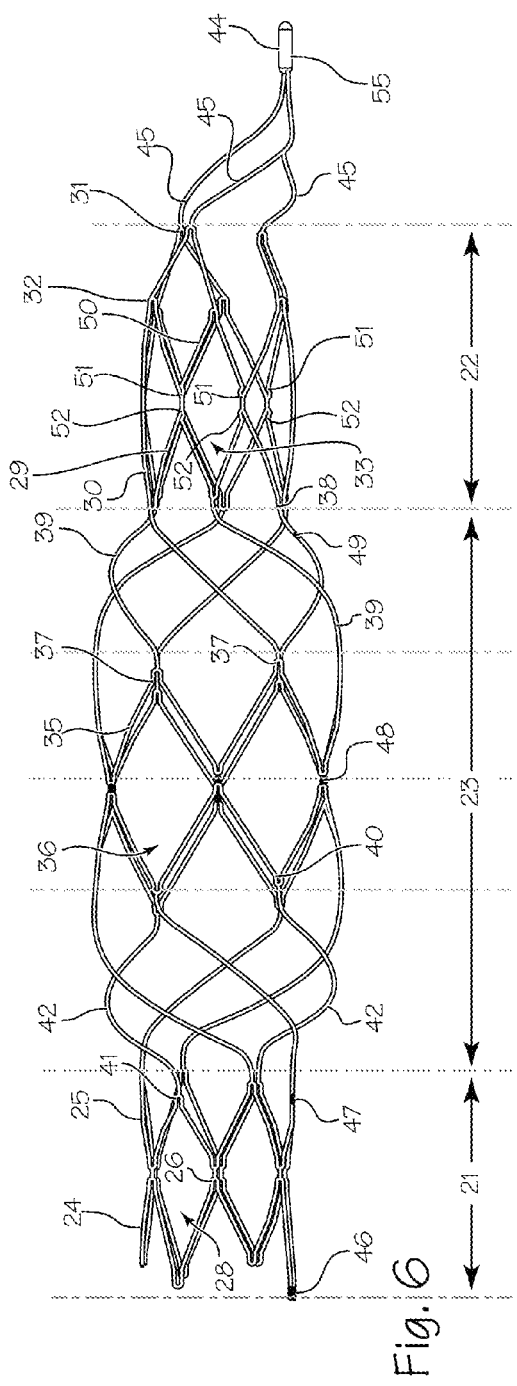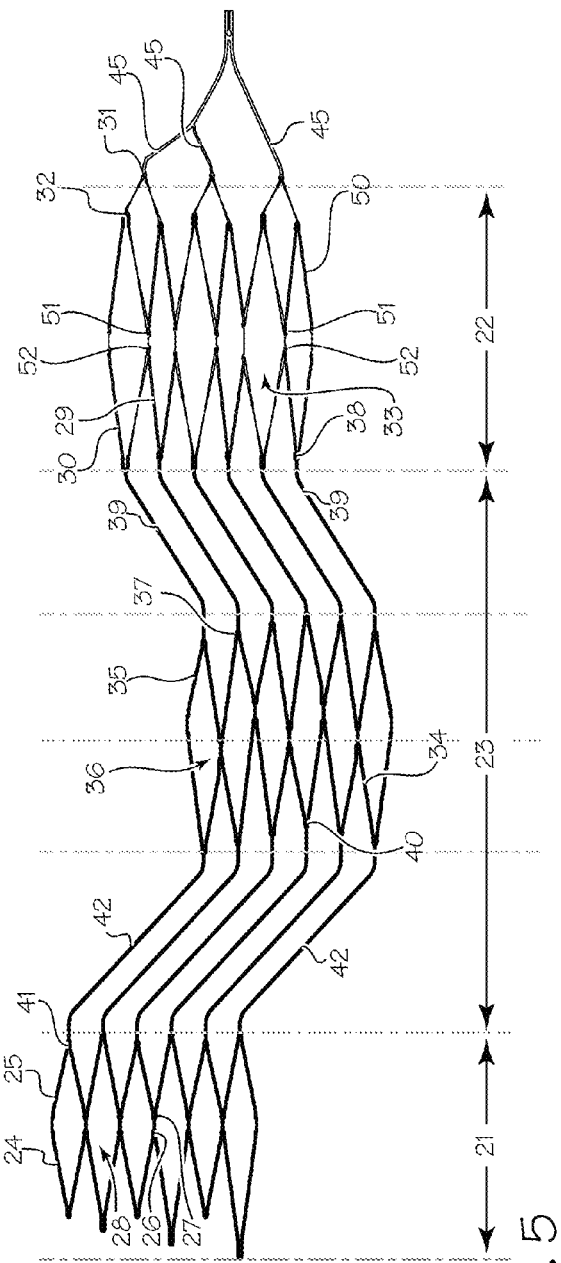
Fig. 6
Fig. 5

PROTUBERANT ANEURYSM BRIDGING DEVICE AND METHOD OF USE

This application claims priority to U.S. Provisional Application 61/556,122 filed Nov. 4, 2011, the entire contents of which are hereby incorporated by reference.

FIELD OF THE INVENTIONS

The inventions described below relate to the field of treatments for wide-necked aneurysms.

BACKGROUND OF THE INVENTIONS

Hemorrhagic stroke accounts for 20% of the annual stroke population. Hemorrhagic stroke often occurs due to rupture of an aneurysm, causing bleeding into the brain tissue and resultant infarction of brain tissue. This can cause immediate death, as well as several well-known neurological defects such as paralysis, loss of sight, hearing or balance. Even if aneurysms in the brain do not rupture, they can cause severe neurological symptoms. Aneurysms may be filled with occlusive material, such as embolic coils, flow modifiers, stents or embolic polymers (ethylene vinyl alcohol, cyanoacrylate, etc.), to prevent rupture and alleviate neurological symptoms. This treatment is promising for many aneurysm in the cerebral vasculature. However, the cerebral vasculature includes many branches and bifurcations where an inlet artery branches into two outlet arteries. Large necked aneurysms (greater than 4 mm, with dome to neck ratios of greater than two) often form at these bifurcations, and the location and openings of these aneurysms often make it difficult to keep occlusive material, once placed in the aneurysm, from falling out of the aneurysm and into the arteries, thus blocking the outlet arteries. This can lead to an embolic stroke, which is just as severe as the hemorrhagic stroke the therapy is intended to prevent.

SUMMARY OF THE INVENTIONS

The devices and methods described below provide for occlusion of a wide necked aneurysm near a vascular bifurcation or trifurcation and placement of an occlusive material in the aneurysm while maintaining or creating a patent flow path for blood to flow from the feeding vessel into both branches of the bifurcation. The device comprises a vessel conforming, protuberant aneurysm bridging device, and is delivered with a delivery system capable of being deployed in the vicinity of a cerebrovascular aneurysm and allow for patent arterial flow while holding embolic material at the neck or slightly herniating into the neck of the aneurysm. The geometry and mechanics of the protuberant aneurysm bridging device are configured to cause retention of the device within the vessel in which the device is placed and maintain patency of the vessels into which the device is placed. The device delivery system is configured to deliver the device, through a microcatheter, with a high degree of accuracy under visualization by fluoroscopy, ultrasound, MRI, or the like. The device delivery system allows for the manipulation and expansion of the protuberant section of the device to conform to the vasculature The protuberant aneurysm bridging device is configured to be placed in a parent vessel, across an aneurysm. The aneurysm can be located within or near a bifurcation. Bifurcation anatomies include the distal end of the basilar artery as well as the location where the middle cerebral artery begins, among many other examples. The protuberant aneurysm bridging device can also be placed across an aneurysm that is not at a bifurcation but formed into the sidewall of a generally non-bifurcated vessel. The protuberant aneurysm bridging device is configured to be coarse enough to allow blood to pass through its open walls but tight enough to keep embolizing coils trapped within an aneurysm such that they cannot protrude out of the aneurysm into the parent vessel or vessels.

The protuberant aneurysm bridging device can comprise a cylindrical first end and a cylindrical second end. The central region of the device can comprise a protuberant, or generally hemispherical, configuration. The central region can comprise a greater open area than the cylindrical first end, the cylindrical second end, or both ends. In other embodiments, the device can be configured with a cylindrical first end having a hollow lumen and be closed at the other ends. The closed other ends can comprise openings between the mesh or strut elements that are larger in some areas than the central areas of the device.

The device can comprise a mesh. In other embodiments, the device can comprise an expanded metal structure formed by slitting or laser-cutting a tube to form struts, for example. The device's mesh or struts can extend slightly into the aneurysm to insure the embolic material is not covering branching arteries.

BRIEF DESCRIPTION OF THE DRAWINGS

FIGS. 3 and 4 illustrate a protuberant aneurysm bridging device for use in bridging a bifurcation aneurysm.

FIGS. 5 and 6 illustrate a protuberant aneurysm bridging device for use in bridging a bifurcation aneurysm with a proximal region modified to provide additional holding power in an inlet vessel.

FIG. 13 illustrates a protuberant aneurysm bridging device side view wherein the device includes a proximal end, a distal end, and several distinct segments there between.

DETAILED DESCRIPTION OF THE INVENTIONS

Figure 1:
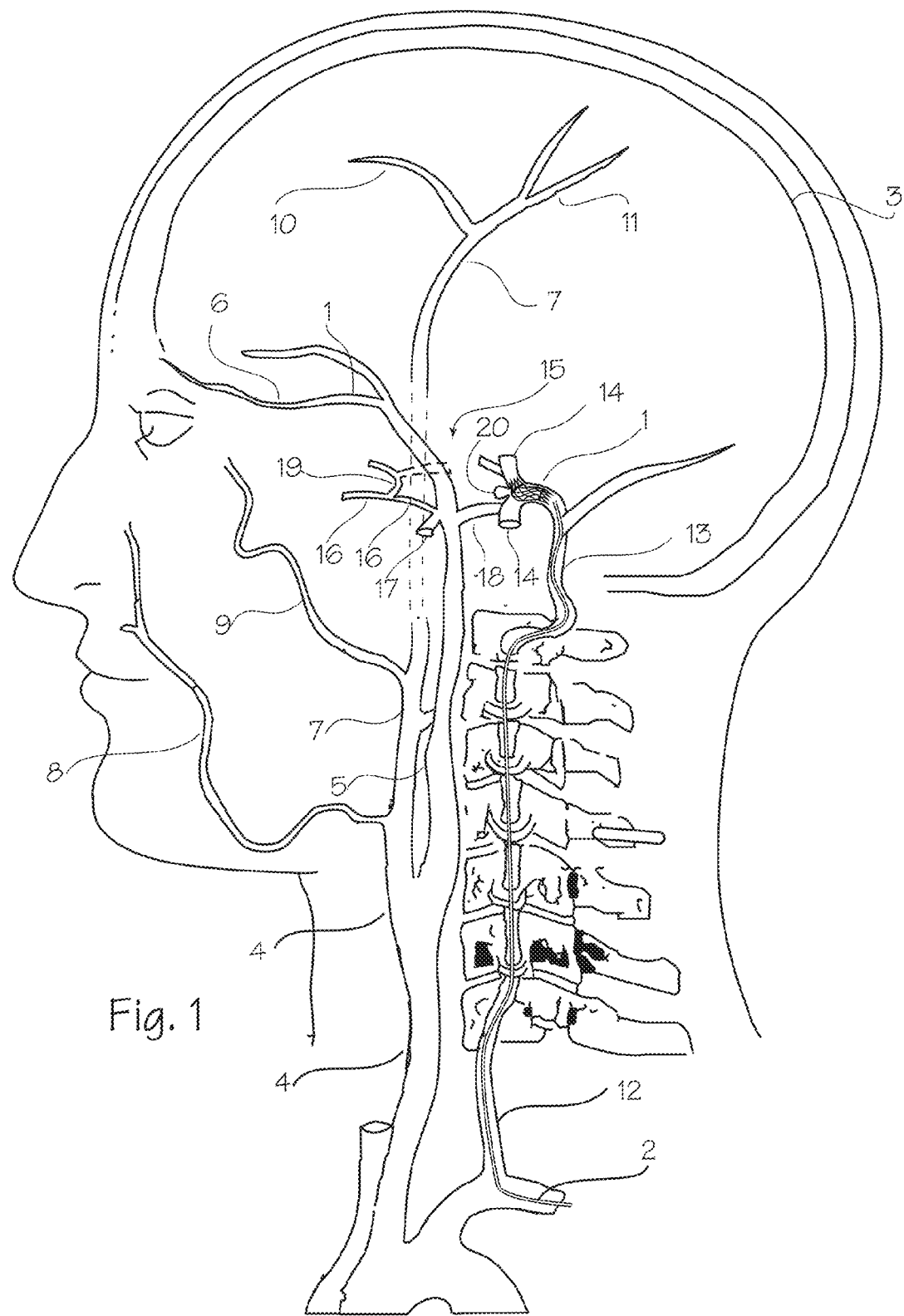
FIG. 1 is a schematic diagram of the vasculature of the brain showing the placement of a protuberant aneurysm bridging device.
Figure 2:
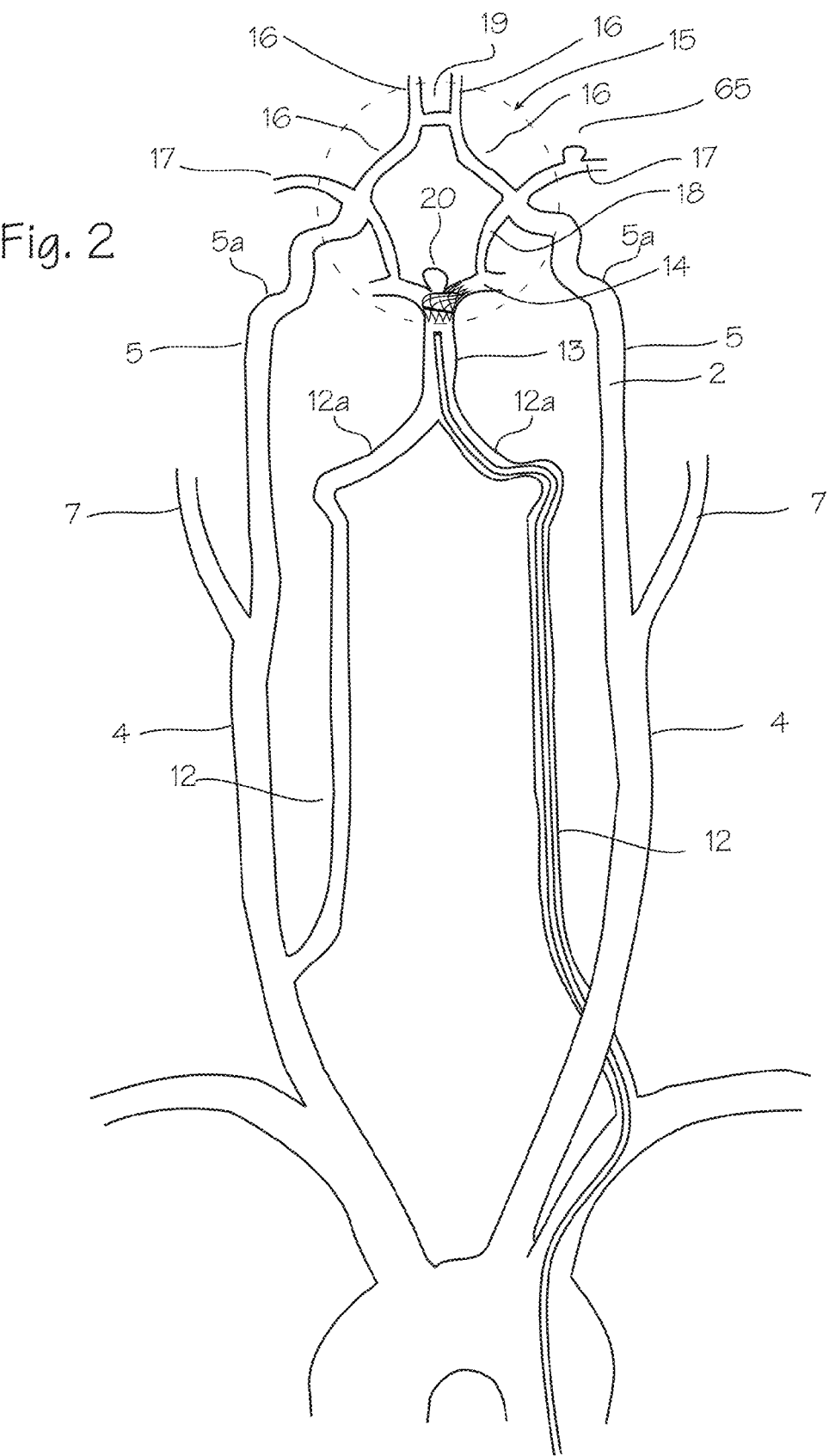
FIG. 2 is schematic diagram of the vasculature of the brain illustrating the circle of Willis and arteries supplying the circle of Willis, also showing the placement of the protuberant aneurysm bridging device.

FIGS. 1 and 2 show the vasculature of the brain in sufficient detail to illustrate the use of the protuberant aneurysm bridging device shown in the following illustrations. The bridging device 1 is shown in an exemplary placement. The bridging device is delivered to this site of a vascular defect with the delivery catheter 2. The neuro-vasculature, which is the intended environment of use for the embolic implant, supplies the brain 3 with blood through the carotid and the vertebral arteries on each side of the neck. The important arteries include the common carotid artery 4 in the neck and the internal carotid artery 5 which supplies the ophthalmic artery 6. The external carotid 7 supplies the maxillary artery 8, the middle meningeal artery 9, and the superficial temporal arteries 10 (frontal) and 11 (parietal). The vertebral artery 12 supplies the basilar artery 13 and the cerebral arteries including the posterior cerebral artery 14 and the circle of Willis indicated generally at 15. The siphon 12a of the vertebral artery appears in the intra-cranial vasculature on the vertebral approach to the Circle of Willis. Also supplied by the internal carotid artery are the anterior cerebral artery 16 and the middle cerebral artery 17, as well as the circle of Willis, including the posterior communicating artery 18 and the anterior communicating artery 19. The siphon 5a of the internal carotid artery 5 appears in the intra-cranial vasculature on the carotid approach into the Circle of Willis. These arteries typically have an internal diameter of about 1 mm to 5 mm, most commonly from 2-4 mm. The methods and devices described herein allow access to these arteries and placement of a bridging device across aneurysm near bifurcations of these arteries. In FIG. 1, the insertion catheter 2 and a bridging device 1 are shown threaded through the common carotid artery 4 and the internal carotid artery 5, which will be a common access pathway for the bridging devices, with the bridging device disposed within the basilar artery 13 and posterior cerebral artery 14, spanning the neck of the basilar tip aneurysm 20.

FIG. 2 shows the same blood vessels in a schematic view that better illustrates the Circle of Willis and the arteries which supply this important anatomic feature. The Circle of Willis 15 is a ring of arteries connecting the internal carotid arteries and the basilar artery (and hence the left and right vertebral arteries) to the anterior cerebral arteries 16, middle cerebral arteries 17 and posterior cerebral arteries 14. The system provides a redundant supply of blood to the cerebral arteries. The carotid siphon 5a, which forms an integral part of the internal carotid artery 5, is more clearly visible in this view. Aneurysms occurring inside the brain, at bifurcations in the intracranial portion of the carotid arteries, vertebral arteries (and the portions of those arteries distal to the siphons) and basilar artery, in the Circle of Willis or even deeper within the brain may be treated with the bridging device and delivery systems described below. FIG. 2 shows an exemplary use in which a delivery catheter 2 is inserted through the vertebral artery to the basilar artery to treat a vascular defect 20 (a basilar tip aneurysm, in this case) with a bridging device.

FIGS. 3 and 4 illustrates a protuberant bridging device for use in bridging a bifurcation aneurysm. The bridging device 1 comprises a stent-like wire-frame structure, substantially tubular in out-line but with most of its wall material removed. The bridging device is highly flexible, compressible and expandable longitudinally, and compressible and expandable radially, and can be manipulated within the vasculature to shape it to obtain a bulbous center while fixing the ends to segments of blood vessel bifurcation on either side of a bifurcation aneurysm. The bridging device is characterized by a distal region 21 and a proximal region 22 and a central region 23. The distal region serves as an anchoring portion, to secure the distal end of the device in a first outlet vessel. The proximal region serves as an anchoring portion, to secure the proximal end of the device in the inlet vessel. The central region serves as a bridging region and a scaffold, to bridge the neck of the aneurysm and hold embolic material in the aneurysm and maintain patency of a second outflow vessel.

The distal region, which corresponds to the distal end of the device (distal referring to the region intended to be disposed deepest within the vasculature (farthest for the origin of an artery), which generally corresponds to the end of the device farthest from the delivery catheter or insertion point in the body) comprises two zigzag segments 24 and 25 disposed with opposing vertices 26 and 27 aligned (the two opposing zigzag segments form a diamond-cell segment 28, characterized by diamond shaped opening between defined by the struts of opposing V-shaped pairs of struts). The zigzag segments are superelastically or resiliently biased to open to the generally cylindrical configuration shown in order to expand to engage the walls artery in which it is place with sufficient compliance mismatch to fix the distal region within the artery.

The proximal region, which corresponds to the proximal end of the device (proximal referring to the region intended to be disposed closest to the origin of an artery, which generally corresponds to the end of the device closest to the delivery catheter or insertion point in the body) comprises a zigzag segment 29 and several V-shaped elements 30 disposed with tops 31 aligned with proximally pointing vertices 32 (forming spaced, non-contiguous diamond-cell segments 33, characterized by diamond-shaped opening defined by the struts of opposing V-shaped pairs of struts). The zigzag segments are superelastically or resiliently biased to open to the generally cylindrical configuration shown in order to expand to engage the walls of the artery in which it is placed with sufficient compliance mismatch to fix the proximal region within the artery. The distal region and proximal region establish a cylindrical structure with dimensions, in their expanded configurations, that match or slightly exceed the diameter of the blood vessel in which they are to be placed. Though V-shaped elements are preferred (for both the distal region and proximal region), the zigzag segments can be configured instead as sinusoidal or wavy segments, with U-shaped elements, for use in larger environments.

The central region 23 is intended to be bulbous, and protrude radially from the cylinder established by the distal end and proximal end, in its expanded configuration. The central region comprises a pair of opposing zigzag segments 34 and 35 with the vertices aligned to meet near the center of the device, again forming a diamond-cell segment 36 (that is, the centrally pointing vertices of the first central zigzag segment 34 are aligned with centrally pointing vertices of the second central zigzag segment 35). This paired zigzag or diamond cell segment is joined, on its proximal end, to the distal end of proximal region. The proximally pointing vertices 37 are connected to the distally pointing vertices 38 of zigzag segment 29 with spirally oriented strut segments 39 which run, along a helical or spiral course relative to the cylinder established by the distal and proximal regions, from the distally pointing vertices 38 to the proximally pointing vertices 37. Likewise, the paired zigzag or diamond cell segment 36 is joined, on its distal end, to the proximal end of distal region. The distally pointing vertices 40 are connected to the proximally pointing vertices 41 of zigzag segment 29 with spirally oriented strut segments 42 which run, along a helical or spiral course relative to the cylinder established by the distal and proximal regions, from the distally pointing vertices 40 to the proximally pointing vertices 41. The zigzag segments and spiral struts are superelastically or resiliently biased to open to the generally cylindrical configuration shown (larger diameter than the distal region and proximal region) in order to expand to engage both the walls of the artery in which it is placed and bridge the open neck of the aneurysm. The spirally oriented struts provide a hinged connection between the central region and both the proximal region and distal region. Because the central region is intended to bulge and protrude from the central axis of the device, it is preferably devoid of additional structures, beyond the spiral struts, zigzag segments and markers, so that it is not constricted from deforming during installation according to the procedure described below.

At the proximal end of the bridging device, the device is removably attached to the delivery wire 43 through an electrolytic detachment joint 44 and several tethers 45. The tethers are additional struts, formed integrally with the remainder of the device, extending around the cylindrical volume established by the proximal region segments, to join the detachment joint along the side of the device. The delivery wire runs through insertion catheter 2.

The bridging device is collapsible to a small diameter configuration which fits inside the distal end of the delivery catheter, and can pass through the lumen of the delivery catheter, for insertion into the body, navigation through the patient's vasculature, and deployment from the distal end. The bridging device, as illustrated, is in its expanded, large diameter configuration, which it assumes after ejection from the distal end of the delivery catheter.

The bridging device includes several radiopaque markers 46 disposed on the distal region. As illustrated, the distal markers are disposed on the distally pointing vertices of the distal-most zigzag segment of the device. Three markers are provided at this longitudinal location, the distal vertices of the distal zigzag segment 24. An additional marker 47 is disposed on a spiral strut near the distal region, marking the proximal extent of the distal region. Several radiopaque markers 48 are disposed at the central vertices of the central paired zigzag segment (in this embodiment, each central vertex is marked with its own marker). Also, a radiopaque marker 49 is disposed near the proximal region, on a spiral strut, marking the distal extent of the proximal region. As illustrated, the proximal marker is disposed on a spiral strut just distal to a distally pointing vertex of the proximal-most zigzag segment of the device. The radiopaque markers facilitate the method of placing the device, which is described below.

FIG. 4 is a schematic illustration of the bridging device of FIG. 3, showing the device as it would appear if opened and splayed out on a flat surface. FIG. 4 shows all the same detail of FIG. 3, and provides an additional view of the zigzag segments, the spiral struts, and the tethers. As can be seen in this Figure, the spiral struts 39 connect a proximally pointing vertices 41 of the distal zigzag segment 25 with a distally pointing vertices 40 of the central region which is circumferentially displaced by at least two other vertices.

As appears from FIGS. 3 and 4 the first central zigzag segment 34 (which opposes the distal region) is characterized by distally pointing vertices, and the second central zigzag segment 35 (which opposes the proximal region) is characterized by proximally pointing vertices. The distally pointing vertices of the first central zigzag segment are joined by the spirally oriented struts 42 extending from an originating distally pointing vertex of the first central zigzag segment to a vertex of the distal zigzag segment 25 which is circumferentially displaced from the originating vertex. Likewise, the proximally pointing vertices of the second central zigzag segment 35 are joined by a spirally oriented strut extending from an originating proximally pointing vertex of the second central zigzag segment to a vertex of the proximal zigzag segment 29 which is circumferentially displaced from the originating vertex. The displacement may be one, two or three vertices or more (using a vertex of the zigzag segments as a unit of measure around the circumference of the device).

FIGS. 5 and 6 illustrate a protuberant aneurysm bridging device for use in bridging a bifurcation aneurysm with a proximal region modified to provide additional holding power in an inlet vessel. This device is modified, vis-à-vis the device shown in FIGS. 3 and 4, with the addition of another zigzag segment 50 in the proximal region. The V-segments of this additional zigzag segment are aligned with the V-segments of the zigzag segment 29, with the distally pointing vertices 51 of zigzag segment 50 aligned with the proximally pointing vertices 52 of the zigzag segment 29. These opposing zigzag segments form a diamond celled segment, which is longer than the corresponding single zigzag segment of FIGS. 3 and 4, and provides additional holding power within the inlet vessel when implanted at a bifurcation. The other elements of bridging device of FIGS. 5 and 6 may be identical to the corresponding elements shown in FIGS. 3 and 4.

Figure 7:
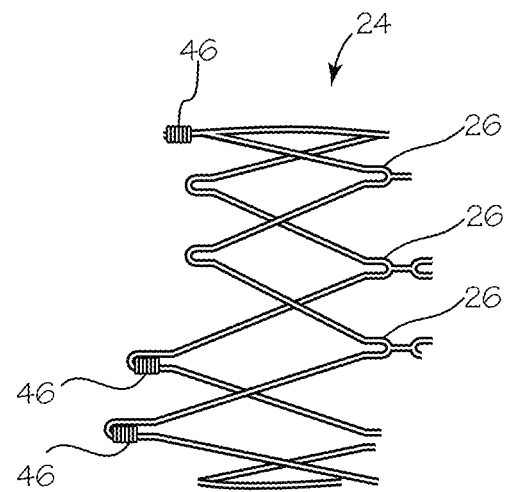
FIG. 7 illustrates the placement of radiopaque markers in various positions on the bridging device.

FIG. 7 illustrates the placement of radiopaque markers in various positions on the bridging device. The markers 46 comprise any radiopaque material, disposed around a small portion of the wire frame structure in the vicinity of the extreme distal tip of the V-shaped elements of the zigzag segment 24. Similar markers are placed at the center region, at the joint between vertices 31 and 32 of the paired zigzag segments 34 and 35, and also at the proximal regions at the distal vertices of the V-shaped elements of the zigzag segment 29.

Figure 8:
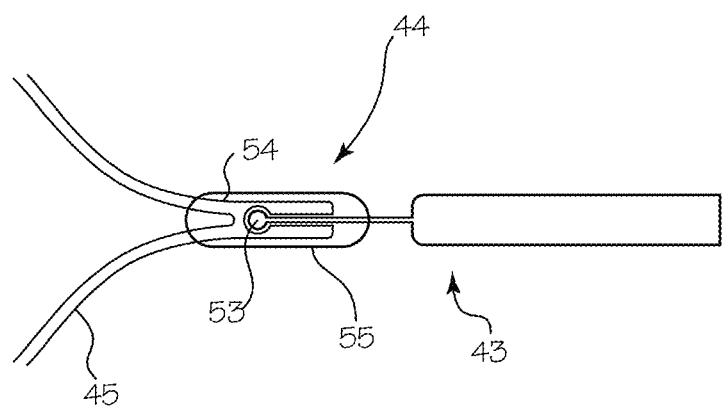
FIG. 8 illustrates the attachment mechanism for securing the bridging device to the delivery wire.

FIG. 8 illustrates the attachment mechanism for securing the bridging device to the delivery wire. The attachment mechanism comprises a detent ball 53 at the distal end of the delivery wire 43 and detent receiver 54 at the proximal end of the tether 45. To attach the bridging device to the delivery wire, the detent ball is forced into the detent receiver. The joint is covered with a radiopaque marker 55. To detach the bridging device from the delivery wire, the electrolytic detachment joint 44 is severed electrolytically, upon application of electrical current to the joint through the delivery wire or associated conductor. Mechanical detachment mechanisms may be used.

FIG. 9a-9g illustrate several steps of delivering the bridging device to the site of a bifurcation aneurysm. The method of treating bifurcations aneurysms is illustrated in these Figures in the basilar tip aneurysm because this is a common wide-necked aneurysm that can be treated with the bridging device. FIG. 9a-9g are set in the Circle of Willis 15, treating a wide-necked aneurysm 20 at the point where the basilar artery 13 divides into the left and right posterior cerebral arteries 18. The procedure will be performed by a surgeon, under visualization with fluoroscopy.

Figure 9A:
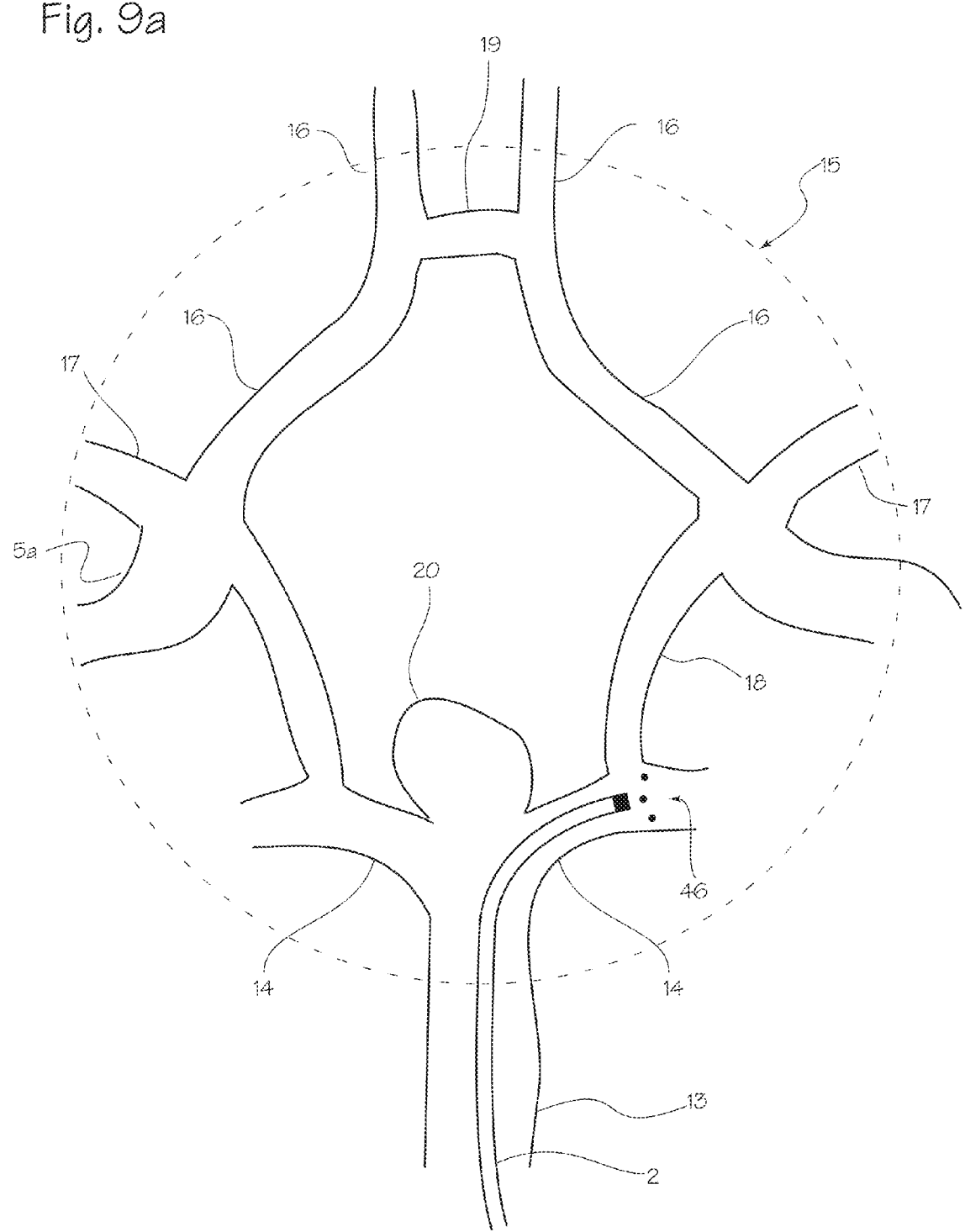
FIG. 9a-9g illustrate several steps of delivering the bridging device to the site of a bifurcation aneurysm.

As shown in FIG. 9a, the surgeon has inserted the delivery catheter 2, with the delivery wire disposed within the catheter, and the bridging device mounted on the distal tip of the delivery wire, through the patient's vasculature so that the distal tip of the catheter 2 is disposed within the posterior cerebral artery 14. With the catheter tip in the posterior cerebral artery 14, the surgeon pulls the delivery catheter proximally, while holding the bridging device distally, partially deploying it from the delivery catheter so that the distal region is outside the catheter and free to expand (superelastically or elastically, depending on the material comprising the device). Upon expansion, the distal region of the bridging device engages the inner wall of the posterior cerebral artery. The release of the distal region from the insertion catheter is seen under fluoroscopy. The struts and wires of the device will likely not be visible under current fluoroscopy systems, so the surgeon will rely on the radiopaque markers. In this first step, the distal set of markers 46 appears outside the delivery catheter, confirming that the distal region is deployed.

Figure 9B:
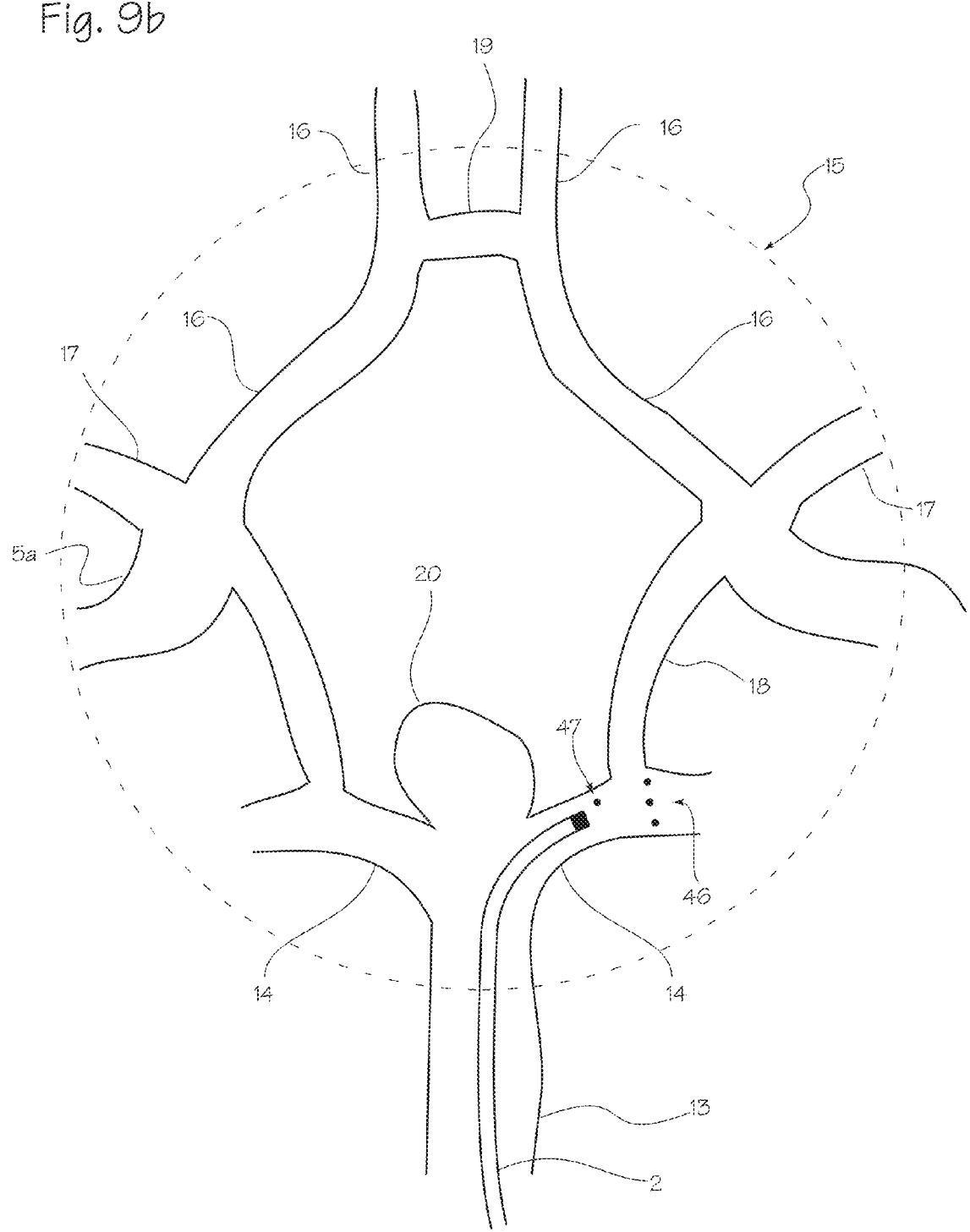

As shown in FIG. 9b, the surgeon has withdrawn the insertion catheter 2 to release the region of the device bearing the radiopaque marker 47, which marks the proximal extent of the distal segment. The surgeon will deploy the device, pulling the device proximally or pushing it distally, to align this distal "edge" marker with the edge of the distal (farthest from the catheter tip) margin of the neck of the aneurysm, at this point or later in the method.

Figure 9C:
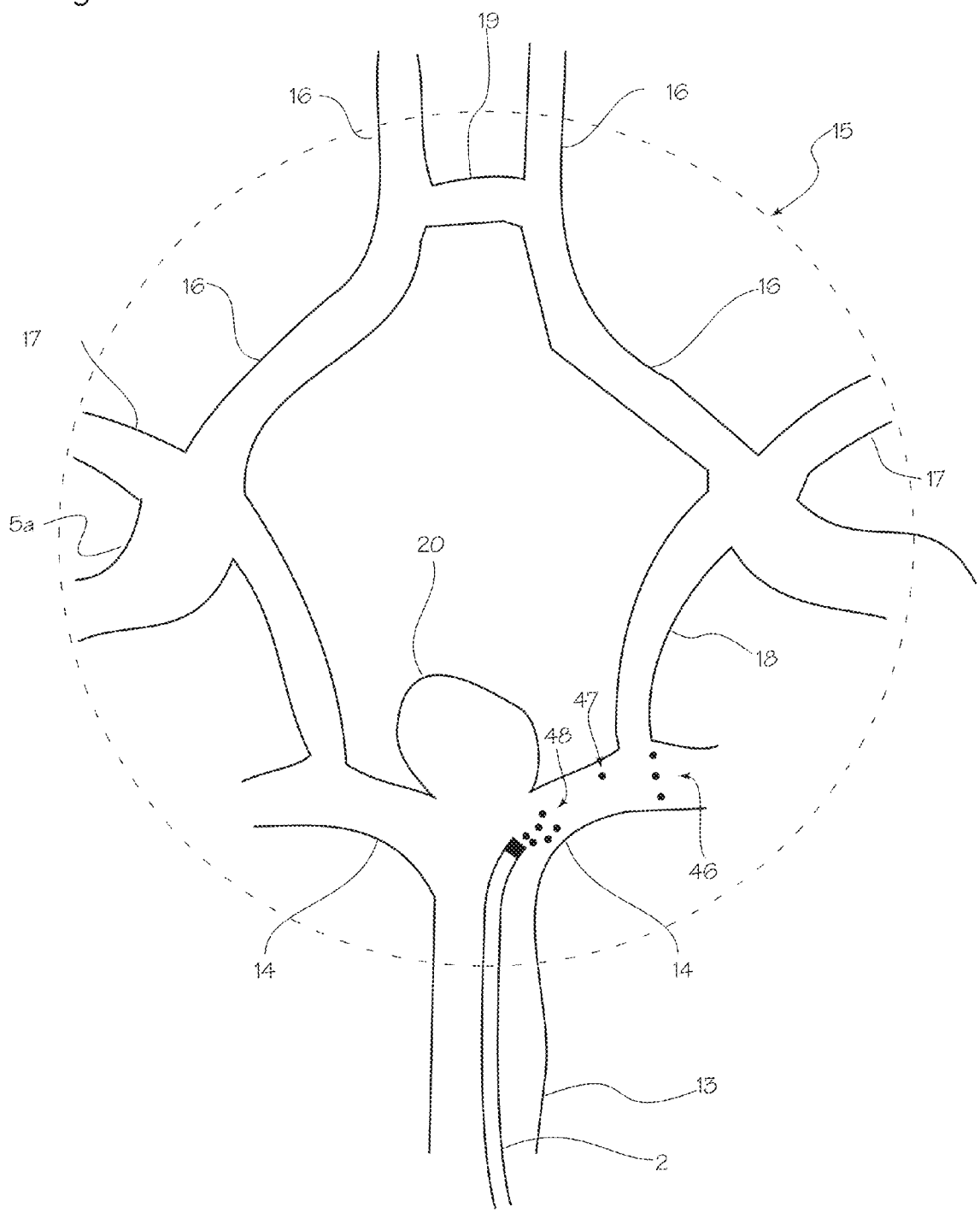

As shown in FIG. 9c, the surgeon has further withdrawn the insertion catheter 2 to release the central region, so that region of the device bearing the radiopaque markers 48 is deployed, and the markers appear on the fluoroscope. All six of the central region radiopaque markers should be visible. The single edge marker is still visible near the distal margin, and the distal markers 46 are visible deeper in the posterior cerebral artery, confirming that the distal region 21 is still properly located.

Figure 9D:
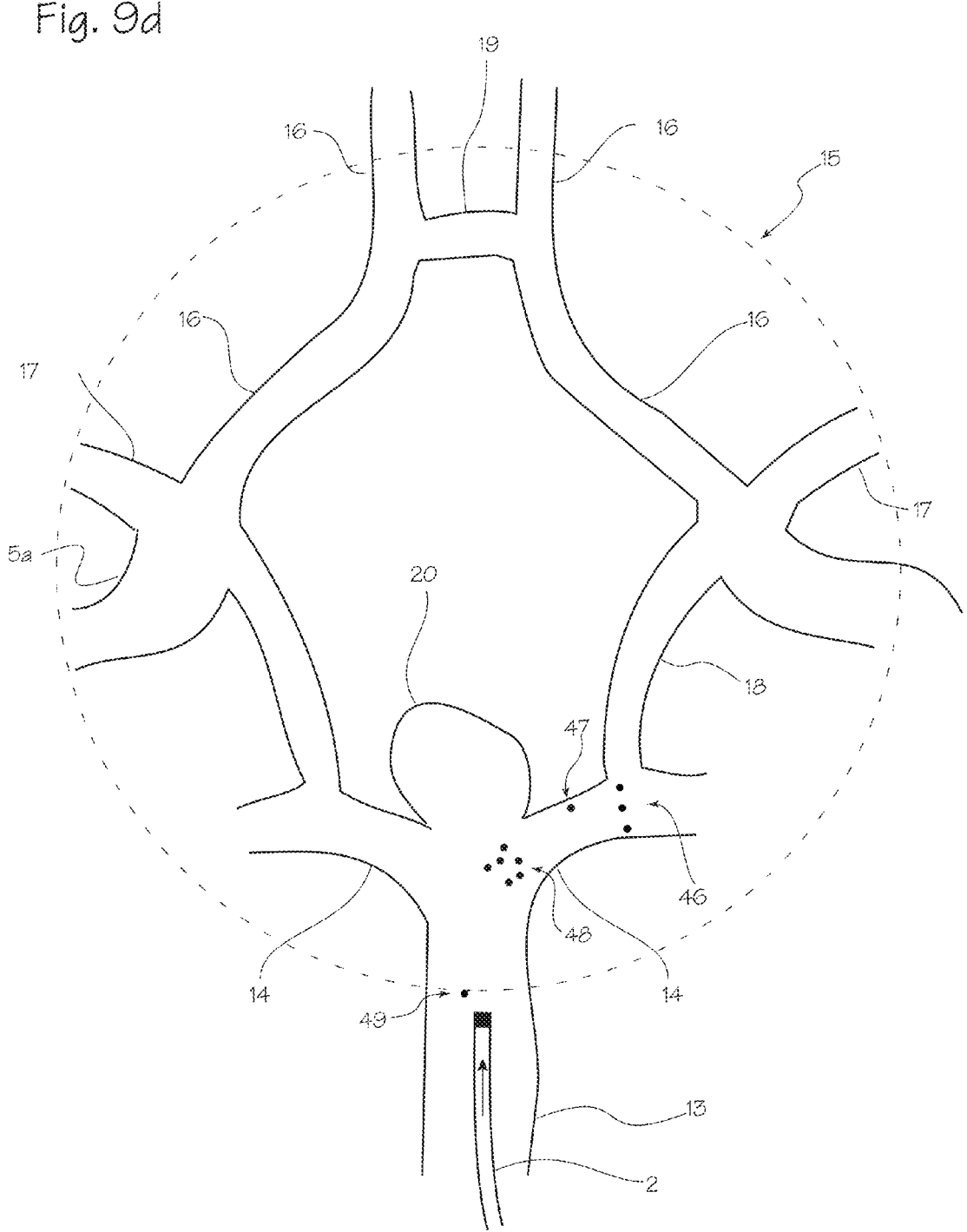

As shown in FIG. 9d, the surgeon has withdrawn the delivery catheter 2 to fully release the central region, so that the proximal radiopaque marker 49 appears on the fluoroscope. The surgeon will manipulate the device, pushing proximally and/or pulling distally, to align this distal "edge" marker with the edge of the proximal (nearest to the catheter tip) margin of the neck of the aneurysm, at this point or later in the method.

Figure 9E:
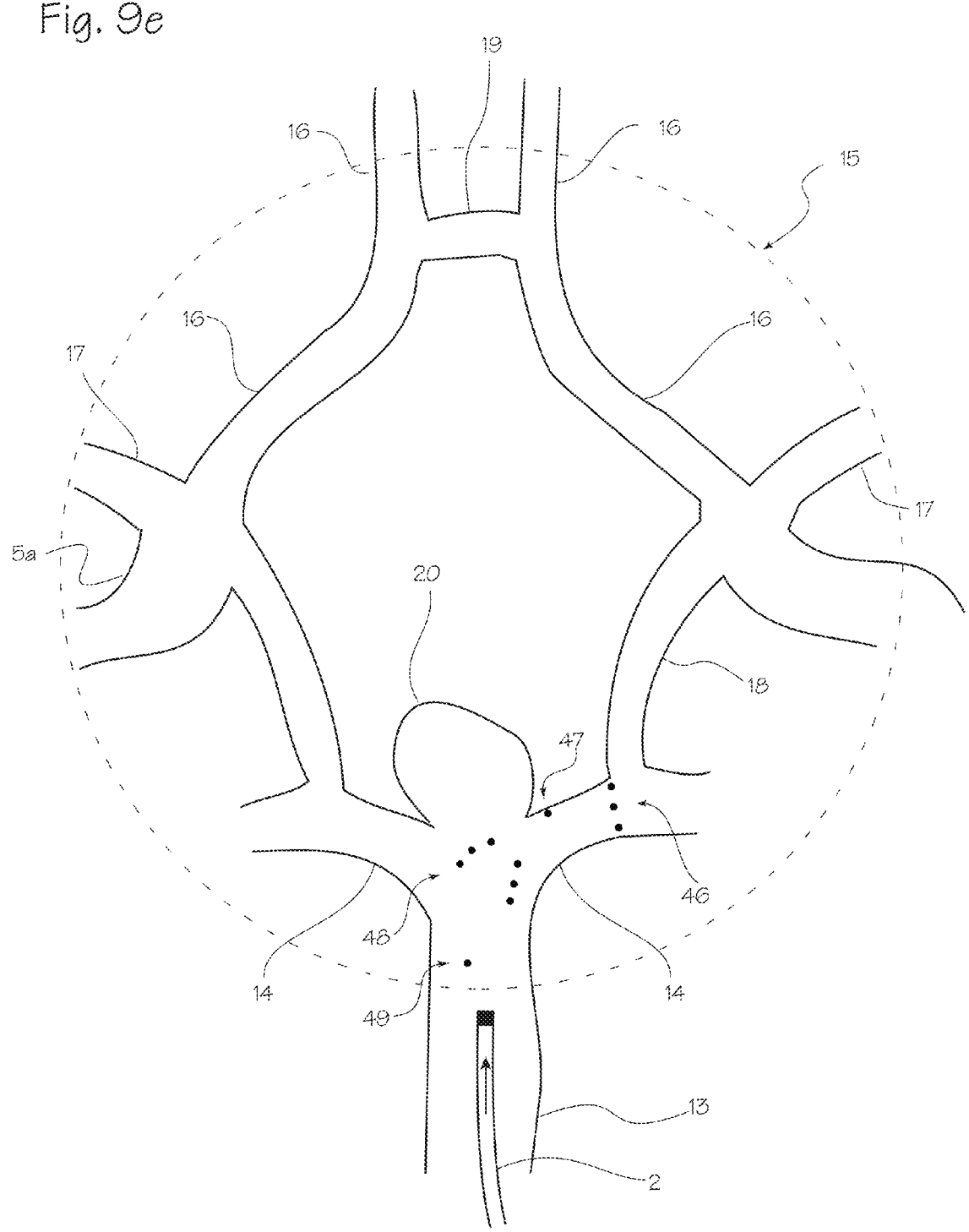

As shown in FIG. 9e, the surgeon has pushed the delivery wire 43 distally, maintaining the delivery catheter 2 in position, to fully release the central region, to push the proximal region distally toward the bifurcation. This results in expansion of the central region, and spreading of the individual spiral struts and zigzag segments through the bifurcation, urging at least one or two of the struts or V-shaped elements into apposition with the aneurysm neck. This is indicated by the movement of the radiopaque markers toward the neck, as illustrated, so that the proximal radiopaque marker 49 appears on the fluoroscope. Again, the single distal edge marker is still visible near the distal margin, and the distal markers 46 are visible deeper in the posterior cerebral artery, confirming that the distal region 21 is still properly located within the posterior cerebral artery.

Figure 9F:
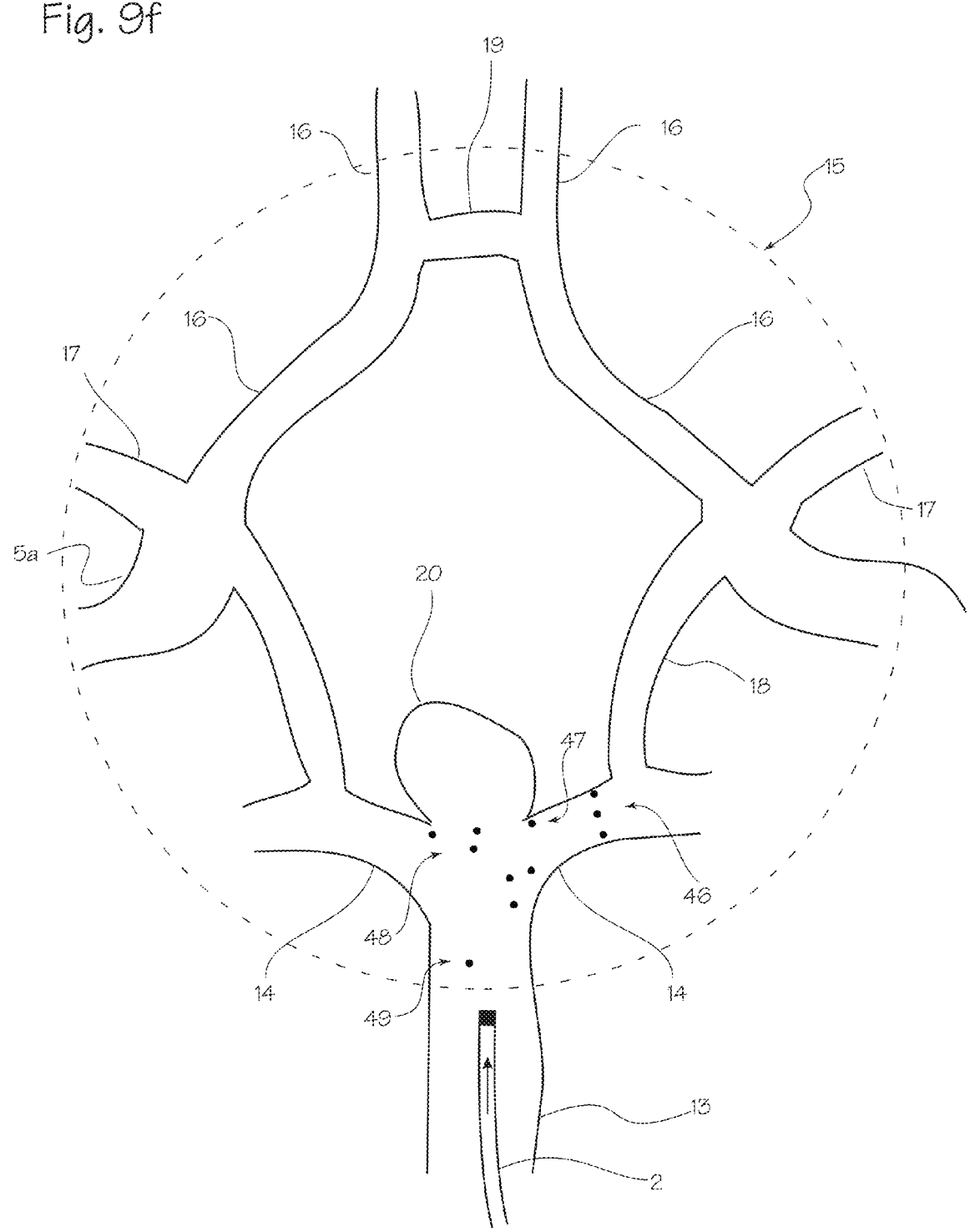

As shown in FIG. 9f, the surgeon has continued manipulated the bridging device with the delivery wire 43, pushing and pulling as necessary to achieve the shape for the central region that best bridges the aneurysm neck.

Figure 9G:
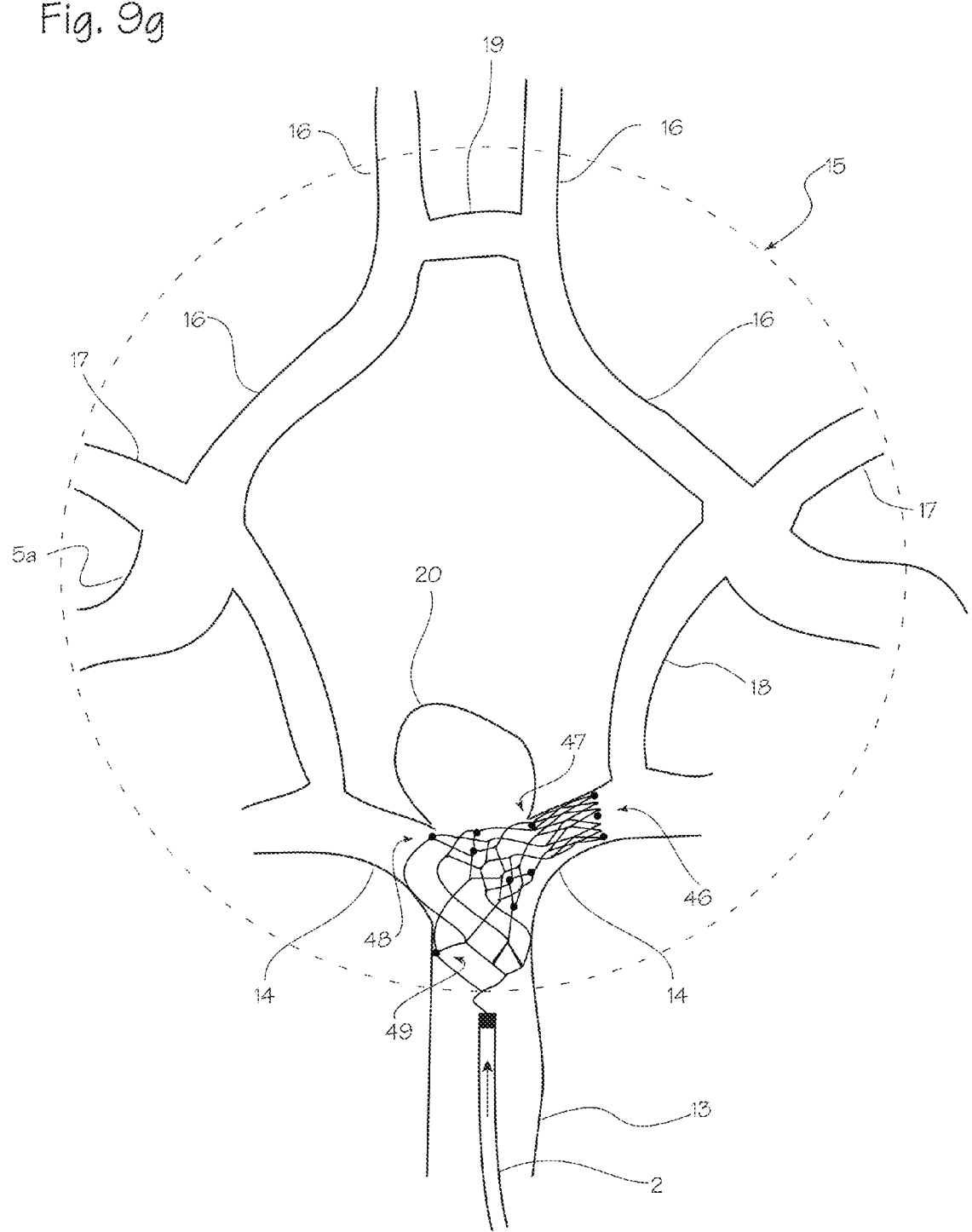
Figure 10:
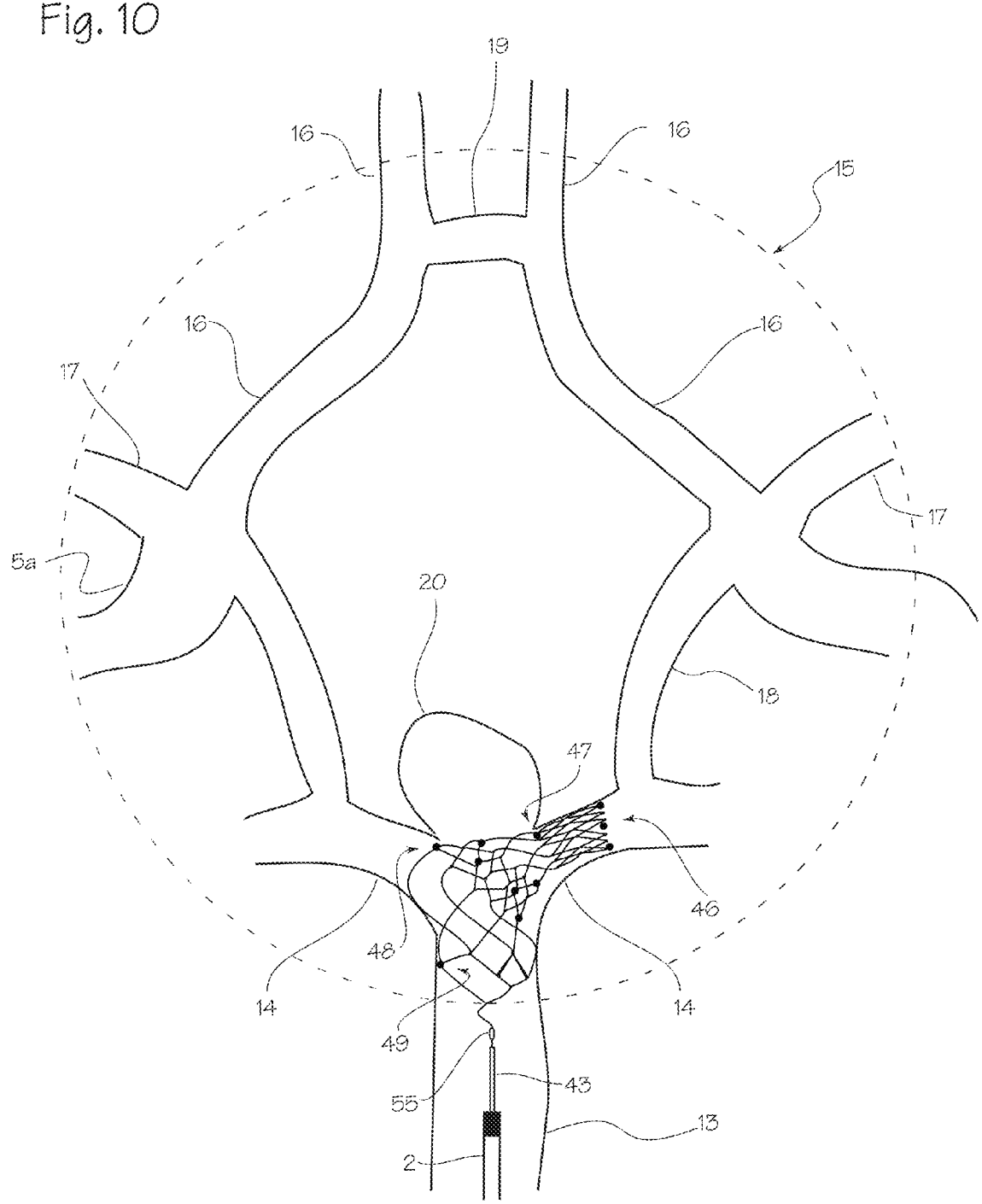
FIG. 10 illustrate the bridging device fully deployed at the site of a bifurcation aneurysm.

As shown in FIG. 9g, the surgeon has withdrawn delivery catheter 2 proximally, to fully release the bridging device, including the radiopaque marker 55 which is fixed that the distal end of the tethers. Further manipulations may be necessary to ensure that the central region struts and V-shaped elements are best located over the aneurysm neck, the distal edge marker is still co-located with the distal edge of the neck, and the proximal radiopaque marker 49 is co-located with the distal extent of the basilar artery. When the surgeon is satisfied with the placement, he operates a power supply connected to the electrolytic detachment joint 44 to sever the delivery wire 43 from the bridging device. Although it will not be visible under current imaging techniques, the bridging device is shown in this FIG. 9g, to illustrate a typical placement. After detachment from the delivery wire, the bridging device is lodged within the bifurcation, with the proximal region expanded to engage the wall of the basilar artery, as shown in FIG. 9g. While permanent implantation will usually be desired, the device may be used as a temporary scaffold to assist in placement of the coils, and the method may be completed in such cases by withdrawing the bridging device into the distal segment of delivery catheter and removing the bridging device from the bifurcation after delivering the occlusive device or substance.

Figure 11:
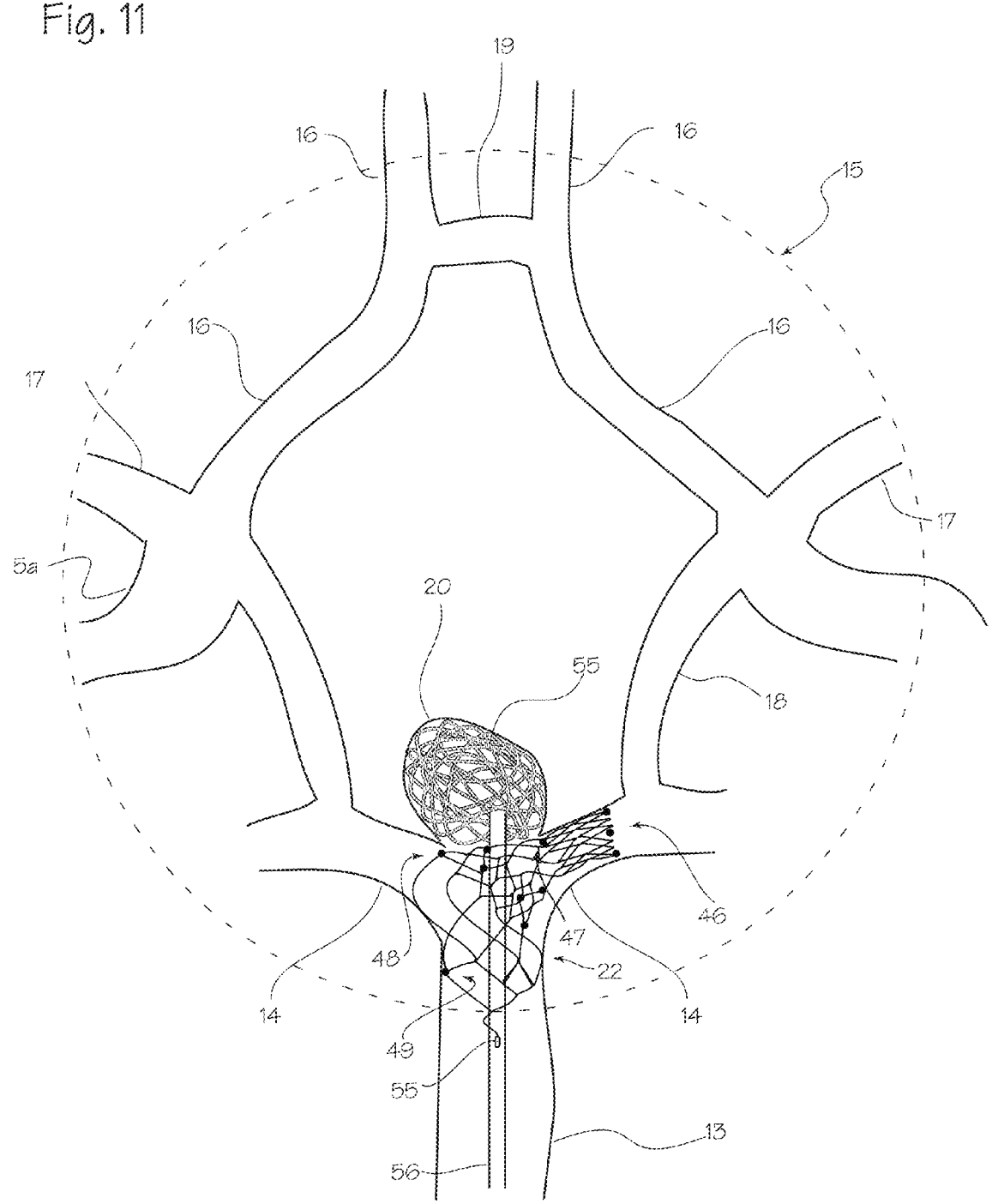
FIG. 11 illustrates the step of filling the aneurysm sac with occlusive material, after placement of the bridging device.

FIG. 11 illustrates the step of filling the aneurysm sac with occlusive material, after placement of the bridging device. As illustrated, the delivery catheter and delivery wire have been withdrawn, and another delivery catheter 56 has been inserted through the vasculature, through the lumen defined by the proximal region 22, out of the device, through spaces between the struts or segments of the central region 23, and into the aneurysm 20. The surgeon will use this catheter to deliver occlusive material, which may include the illustrated embolic framing coil 57, embolic coils, hydrocoils, or embolic substances. After placement of the embolic material, the central struts and V-shaped elements which protrude from the main axis of the device (relative to the diameter established by the distal and proximal regions) will act as scaffolds to hold the embolic material (especially the finest embolic coil loops) in place and prevent it from dropping out of the aneurysm sac to occlude the opposite posterior cerebral artery.

Though the method is illustrated with specific reference to the basilar tip aneurysm, which occurs at the terminus of the basilar artery, the method can be used to treat bifurcation aneurysms at bifurcations of the middle cerebral artery 17, the internal carotid artery 5, the anterior communicating artery 19 (at the anterior cerebral artery 16), the superior cerebellar artery, the pericallosal artery (a continuation of the anterior cerebral artery), the posterior inferior cerebellar artery, or any other bifurcation. Each bifurcation is characterized by an inlet artery, and first outlet artery and a second outlet artery, which in the illustration of FIGS. 9a through 9g correspond to the basilar artery, the left posterior communicating artery and the right posterior communicating artery.

Figure 12:
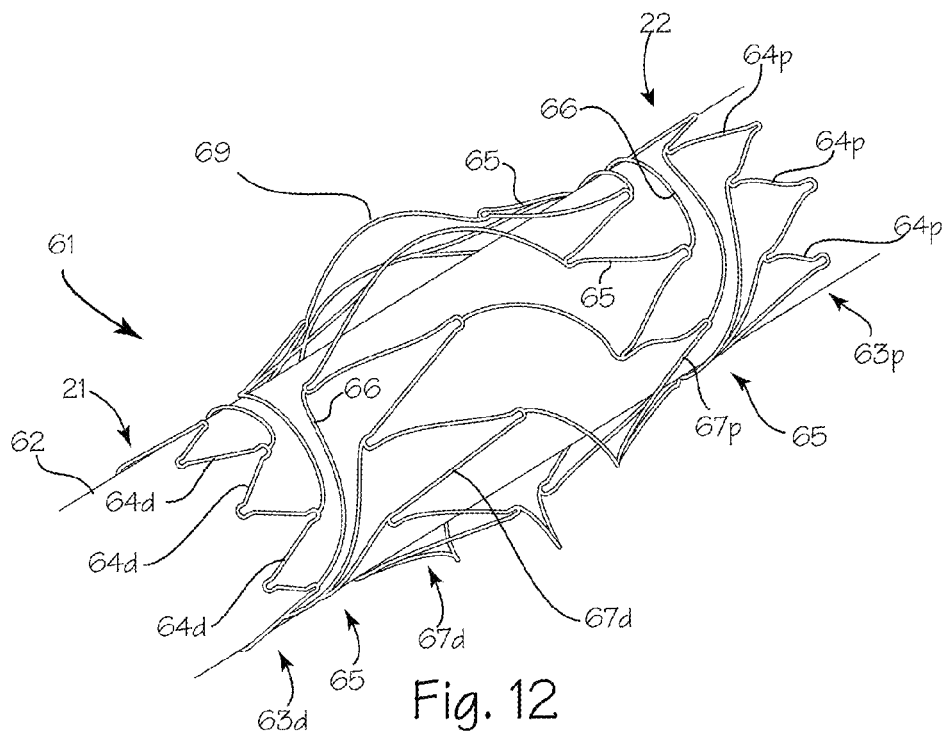
FIG. 12 illustrates a protuberant aneurysm bridging device following initial forming being wrapped around a construction mandrel for final shaping.
Figure 13:
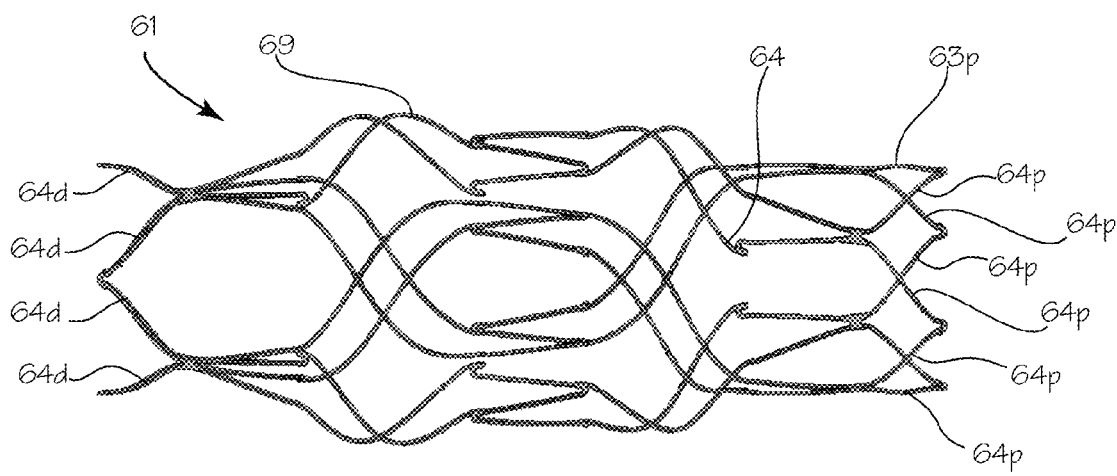

The bridging device can be made various configurations in which the number of zigzag segments is varied, the length of the segments or the length of the spiral struts is varied, or the number of V-shaped elements in the various zigzag segment is varied. These various embodiments are described in the following figures. FIG. 12 illustrates an embodiment of a protuberant aneurysm bridging device 61 assembled over a mandrel 62. The device 61 comprises a distal end region 21, comprising a zigzag segment 63d comprising V-shaped segments 64d and a proximal end region 22 comprising a zigzag segment 63p comprising V-shaped segments 64p, and a central region 23. The central region comprises two first intermediate spiral strut regions 65, each comprising a plurality of first intermediate spirally oriented struts 66, two second intermediate zigzag segments 67d and 67p each with a plurality of second intermediate V-shaped struts 68, and a plurality of spirally oriented center struts 69 joining vertices of the zigzag segment of the second intermediate V-shaped struts on either end of the spirally oriented center struts. This protuberant aneurysm bridging device can be symmetric about an axis running laterally to the longitudinal axis. FIG. 13 illustrates a side view of the protuberant aneurysm bridging device 61 clarifying the end regions 63d and 63p, the central region 69, and first intermediate strut regions 65. The spirally oriented struts that join each of the zigzag segments extend, as described in relation to the spirally oriented struts of FIGS. 3 and 4, circumferentially around the volume defined by the device, from a vertex of one zigzag segment to a vertex of the next zigzag segment which is circumferentially displaced from the originating vertex. The displacement may be one, two or three vertices or more (using a vertex of the zigzag segments as a unit of measure around the circumference of the device).

The protuberant aneurysm bridging device 61 is fabricated by cutting a pattern. The pattern can be cut into a flat sheet of device material which is then rolled and the ends affixed to each other. The flat sheet embodiment can be fabricated using laser cutting, electrical discharge machining (EDM), wire EDM, photochemical etching, mechanically machined, or otherwise machined. In other embodiments, the device 61 can be cut from a tubular blank using methodology itemized above for the flat sheet embodiment.

The protuberant aneurysm bridging device 61 can be fabricated from materials such as nitinol, shape memory nitinol, martensitic nitinol, superelastic or pseudoelastic nitinol, stainless steel, titanium, cobalt nickel alloys, tantalum, and the like. The device 61 can be malleable or it can be elastically biased outward to be self-expanding.

Following machining, the protuberant aneurysm bridging device 61 can be expanded or dilated from a first, smaller inside diameter, to a second, larger inside diameter. The device 61 can next be temporarily affixed about the mandrel 62. The device 61 can next be selectively twisted to expand and re-configure specific regions, especially the spiral regions such as the central region 69 or one or both of the first intermediate regions 65. The device 61 can next be heat set to retain its shape. For example, when made of superelastic nitinol, the device 61 is fabricated from nitinol which can be heat set at temperatures of about 450° C. to about 550° C. while maintained in a specific shape, after which the temperature and restraint can be removed leaving the device in its final, unstressed configuration. Optional quenching, such as with water, can be used to rapidly cool the device 61. The heat set time can range from about 1 minute to about 15 minutes depending on mass, material, and temperatures used. FIG. 12 illustrates one of many configurations possible for a device using different flat patterns, different materials, different numbers of struts, and different strut thicknesses, widths, and lengths. The number of struts can vary between about 6 and about 16 or more, and preferably between about 8 and 14, with a generally similar number of slots interspaced between the struts.

Figure 14:
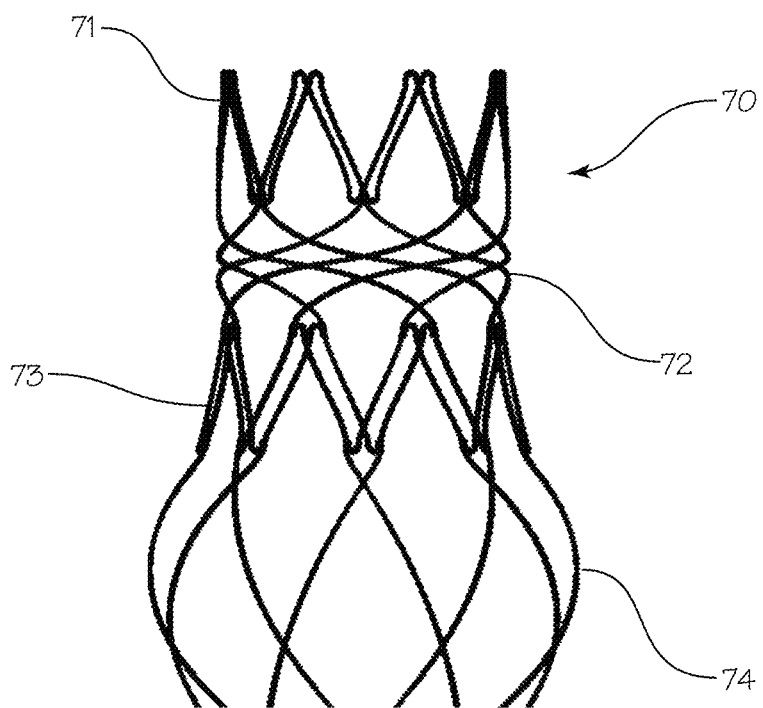
FIG. 14 illustrates one end of a protuberant aneurysm bridging device wherein the device includes an end segment, a first intermediate segment, a second intermediate segment, and a central segment.

FIG. 14 illustrates a side view of the distal end of a protuberant aneurysm bridging device 70 comprising an end region 71, a first intermediate region 72, a second intermediate region 73, and a central region 74. In this configuration the device 70 is generally the same or similar as that of the device 61 of FIG. 12.

Figure 15:
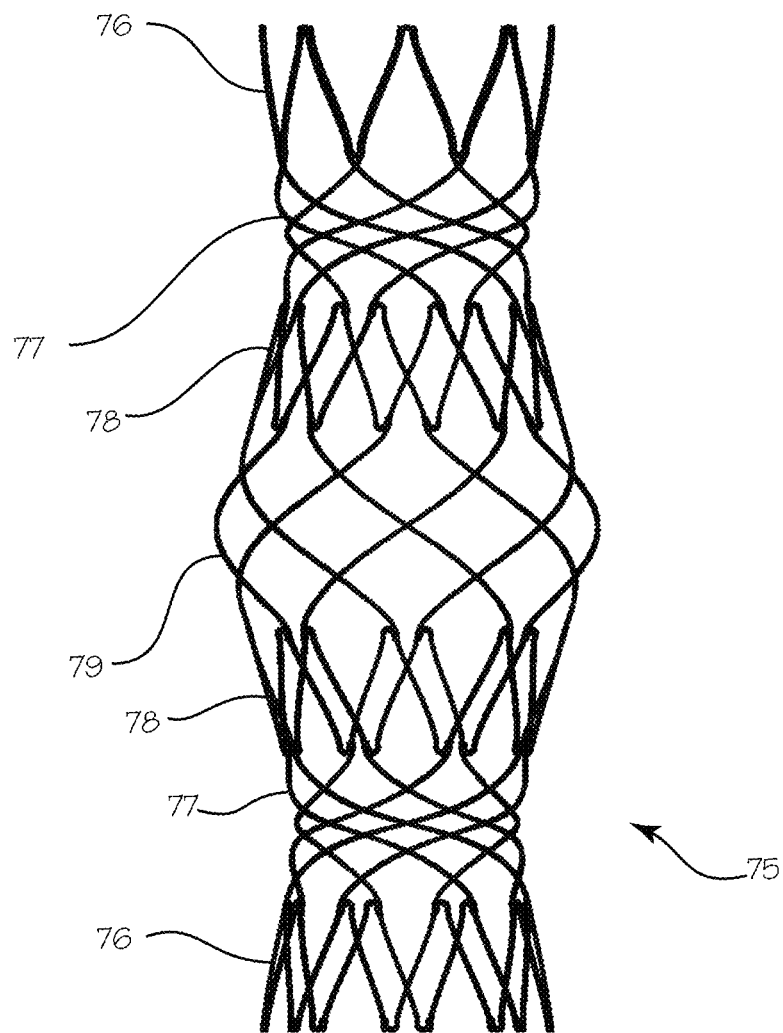
FIG. 15 illustrates a complete protuberant aneurysm bridging device formed in the manner of the device of FIG. 14 but showing all the device segments.

FIG. 15 illustrates a side view of a protuberant aneurysm bridging device 75 comprising two end regions 76, two first intermediate regions 77, two second intermediate regions 78, and a central region 79.

Referring to FIG. 15, the two first intermediate regions 80 are configured to provide bending out of the longitudinal axis. The central region 81 is further configured for axial bending. The two end regions 82 and the two second intermediate regions 83 comprise zigzag segments, maintain partial diamond, diamond, or wave structures that are generally stiff and resist bending out of the longitudinal axis but provide superior hoop strength and holding power within an artery or vessel. Furthermore, the central region 79 is generally loosely configured with large spaces between struts or elements and permits blood flow therethrough. The first intermediate regions 77 are further configured for greater open space than the end regions 76 or the second intermediate regions 78. The first intermediate region 77 can be beneficial when placed across a bifurcation or trifurcation outlet vessel and permit continued blood flow without embolization. The end regions 76 can be configured, as illustrated, with an outward taper to facilitate holding within the vessel wall.

Figure 16:
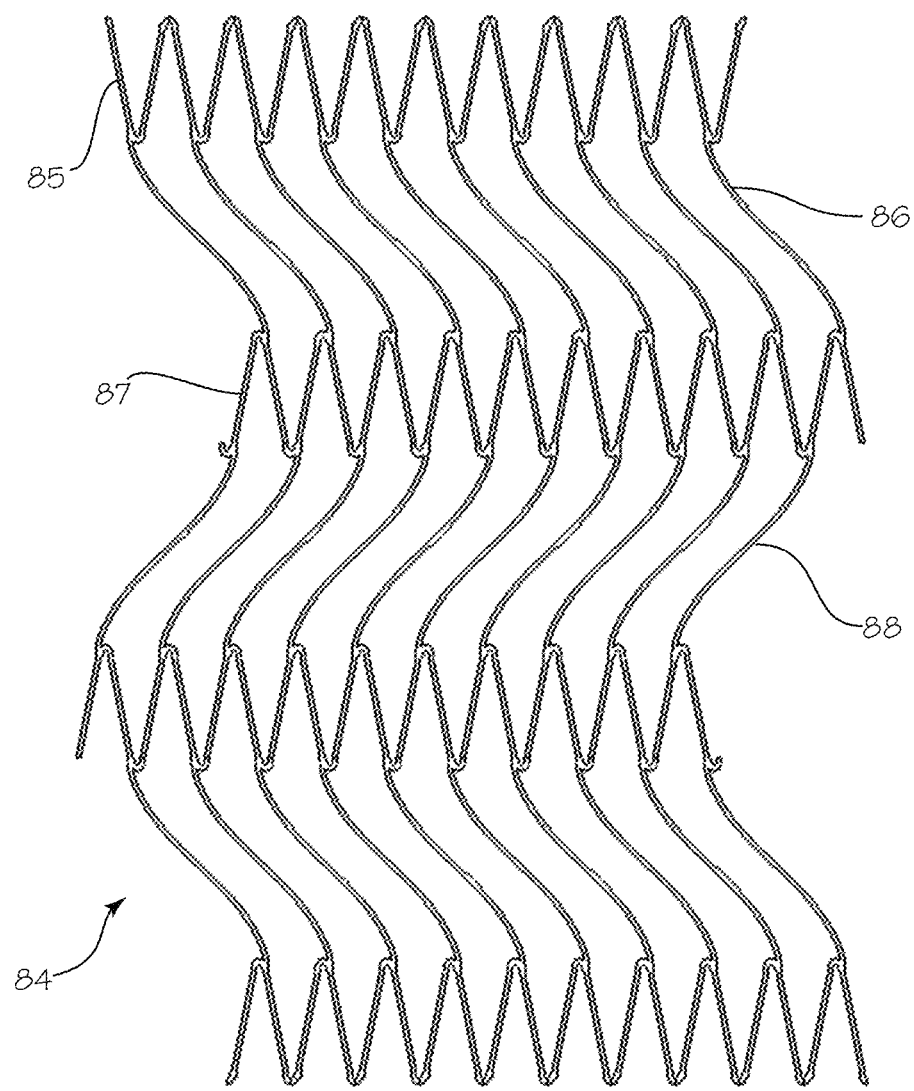
FIG. 16 illustrates a flat pattern diagram of a protuberant aneurysm bridging device wherein the device is fabricated from a flat sheet of material and before any forming of intermediate segments.

FIG. 16 illustrates a flat pattern 84 corresponding to the tubular protuberant aneurysm bridging device 61, 70 or 75. The flat pattern 84 comprises a plurality of end bars 85, a plurality of first intermediate bars 86, a plurality of second intermediate bars 87, and a plurality of central bars 88. In FIG. 16, the flat pattern 84 comprises a plurality of repeating patterns, for example 10 repeat patterns in the lateral direction, but this number can vary as described herein. The end regions 85 are formed as undulations or "V" patterns interconnected to each other. The end regions 85 can also be formed as a plurality of approximately diamond-shaped patterns. The end regions 85 are interconnected at their interior ends to the outside ends of the first intermediate region bars or struts 86. In the device of FIG. 16, the inner ends of the first intermediate struts 86 are connected to the outer ends of the second intermediate struts 87 but the connection is not symmetrical but slightly off-center of the arc connecting the "V" patterns. The first intermediate struts are configured with a slight wave but can also be straight, more strongly "S" shaped, or shaped in some other suitable wave or geometric pattern. This flat pattern 84 can be used to program a cutting system to create the pattern in a tubular blank. Alternately, this flat pattern 84 can be fabricated into a flat sheet of material which is then rolled circumferentially and the ends welded or otherwise affixed.

In the illustrated embodiment, a preferred specification provides for three longitudinal cells and ten repeat patterns circumferentially. The width of the bars is about 65 micrometers and the wall thickness of the material is about 74 micrometers. The illustrated flat pattern 84 can be suitable for, or cut from, a tube having a diameter of about 2.464 mm. The diameter of the tubing blank can vary depending on the application. The wall thickness can vary from about 0.25 mm to about 0.5 mm to about 0.20 mm. The bar or strut width can vary from about 0.25 mm to about 0.1 mm with a preferred range of about 0.3 mm to about 0.5 mm.

Figure 17:
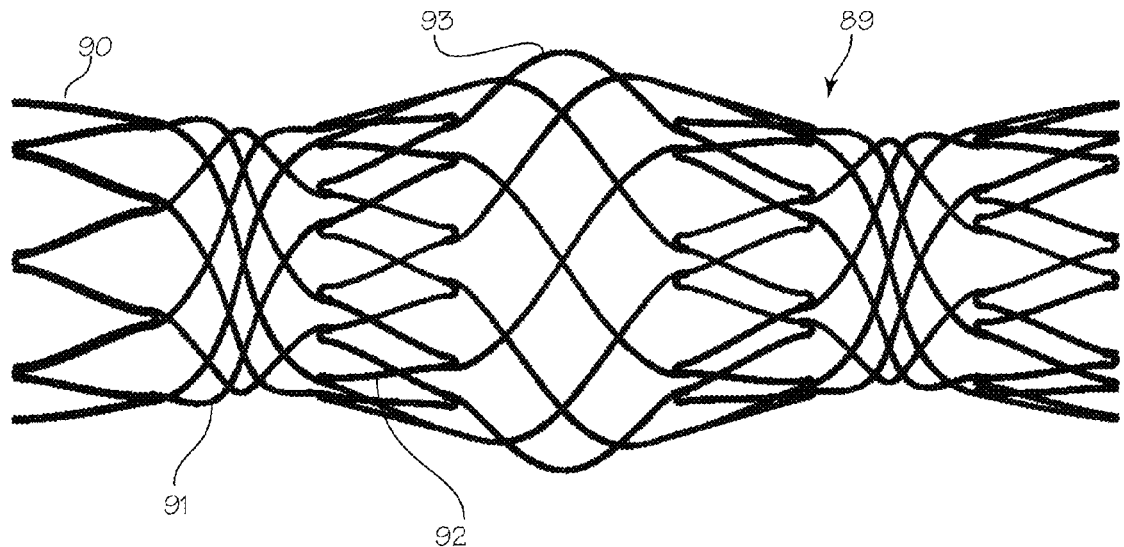
FIG. 17 illustrates a protuberant aneurysm bridging device fabricated from the flat pattern of FIG. 13 and formed around an axially elongate cylindrical shape with further forming generating different patterns in the proximal and distal first intermediate segments as well as the central segment.

FIG. 17 illustrates a protuberant aneurysm bridging device 89 fabricated from a flat pattern similar to, or the same as, that illustrated in FIG. 16. The device 89 comprises two end sections 90, two first intermediate sections 91, two second intermediate sections 92, and a central section 93. The wavy patterns in the end sections 90 are relatively large with large strut lengths. The overall length of the device 89 is about 15 mm but this length can vary between about 8 mm and about 25 mm.

Figure 18:
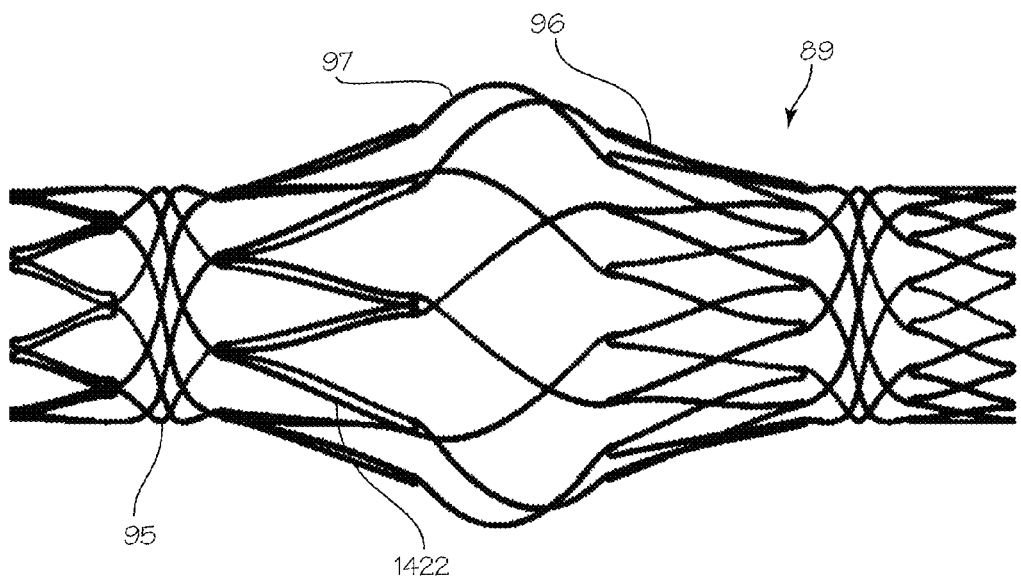
FIG. 18 illustrates a protuberant aneurysm bridging device fabricated into its cylindrical shape but having larger length second intermediate segments and shorter length end segments.

FIG. 18 illustrates a protuberant aneurysm bridging device 89 comprising two end sections 94 and a central region comprising two first intermediate sections 95, two second intermediate sections 96, and a central spiral strut section 97. The wavy patterns in the end sections 94 are relatively short and provide for a stiffer end section 94 than in the end sections 90 of the device 89. The second intermediate sections 96 are relatively long compared to the second intermediate sections 96 of the device 89 of FIG. 17. These types of strut length changes are typically performed at the stage of fabricating the flat pattern such as in FIG. 16. The overall length of the device 89 is about 15 mm but can range from about 8 mm to about 25 mm. The central region 97 and the two secondary intermediate regions 96 together comprise a length of about 10 mm but this length can vary between about 5 mm and about 15 mm. The outside diameter of the two end sections is about 4 mm in FIG. 18 but this diameter can vary between about 2 mm and about 6 mm. The diameter of the enlarged central region, at its greatest is about 8 mm but can vary between about 3 mm and about 12 mm.

Figure 19:
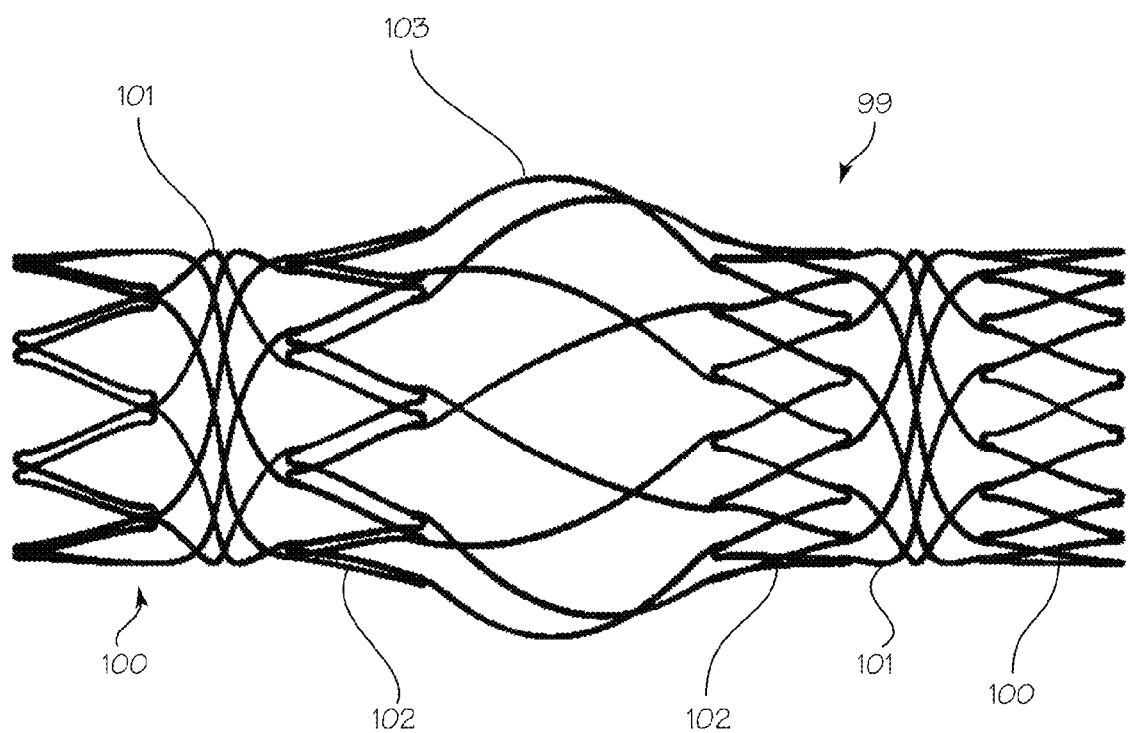
FIG. 19 illustrates a protuberant aneurysm bridging device fabricated into an axially elongate cylindrical shape with shorter second intermediate segments than the device of FIG. 18.

FIG. 19 illustrates a side view of a protuberant aneurysm bridging device 99 comprising two end sections 100 and a central region comprising two first intermediate sections 101, two second intermediate sections 102, and a central spiral strut section 103. The device 99 comprises second intermediate regions 102 which have shorter struts than those 96 of device 89 and about the same as the intermediate regions 92 of device 89. However the central region 103 is longer than the central region 97 of device 89 and about the same as the central region 93 of device 89. The overall length of the protuberant aneurysm bridging device 99 is about 15 mm but can vary between about 8 and 25 mm. The central region 103 and the two secondary intermediate regions 102 comprise about 8.5 mm length but this can vary between about 5 mm and about 15 mm. The overall diameter of the unstressed, expanded central region 103 is about 6 mm but can vary between about 4 mm and about 12 mm. The outside diameter of the end regions 100 is about 4 mm with a range of about 2 mm to about 8 mm.

Figure 20:
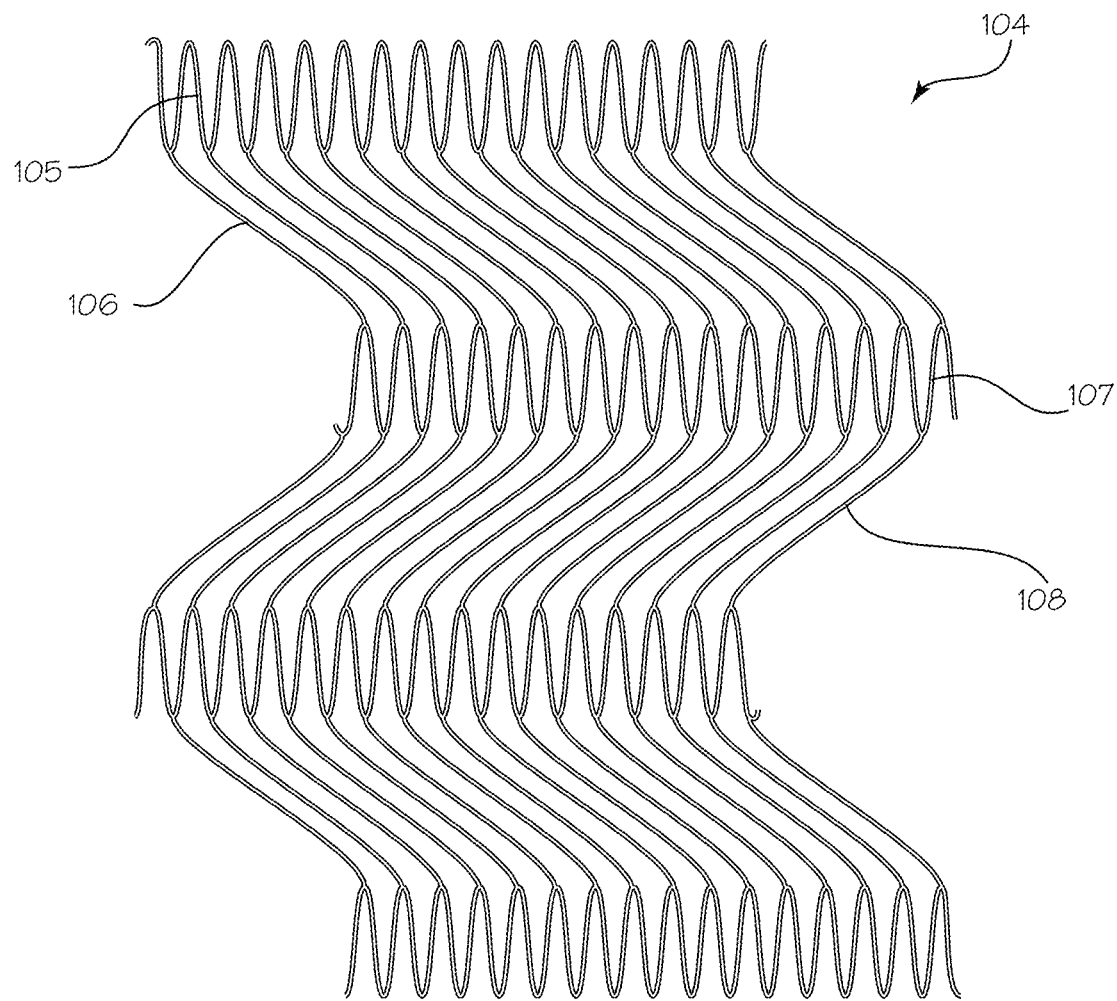
FIG. 20 illustrates a flat pattern of a protuberant aneurysm bridging device similar to the flat pattern of FIG. 13 except that the two first intermediate segments and the central segment are longer and more laterally disposed than that of the flat pattern of FIG. 16.

FIG. 20 illustrates a flat pattern 104 of a protuberant aneurysm bridging device comprising 16 repeat patterns in the circumferential direction. The flat pattern 104 comprises two end regions 105 and a central region comprising two first intermediate regions 106, two secondary intermediate regions 107 and a central spiral strut region 108. The flat pattern 104 is denser in the circumferential direction than the flat pattern 84 since it has more struts. The flat pattern 104 comprises three cells, wherein two cells comprise an end region 105 and a secondary intermediate region 107 as well as the connecting first intermediate region 106. The third cell comprises the central region 108 and the two secondary intermediate regions 107. The tube diameter preferred for this configuration is about 2.462 mm on the outside but can range from about 1 mm to about 4 mm. The wall thicknesses are similar to those specified for the flat pattern 84 in FIG. 16. The bar widths would generally be somewhat smaller for the embodiment 104 than in the flat pattern 84 since there are more bars (and spaces) in flat pattern 104 than in flat pattern 84.

Figure 21:
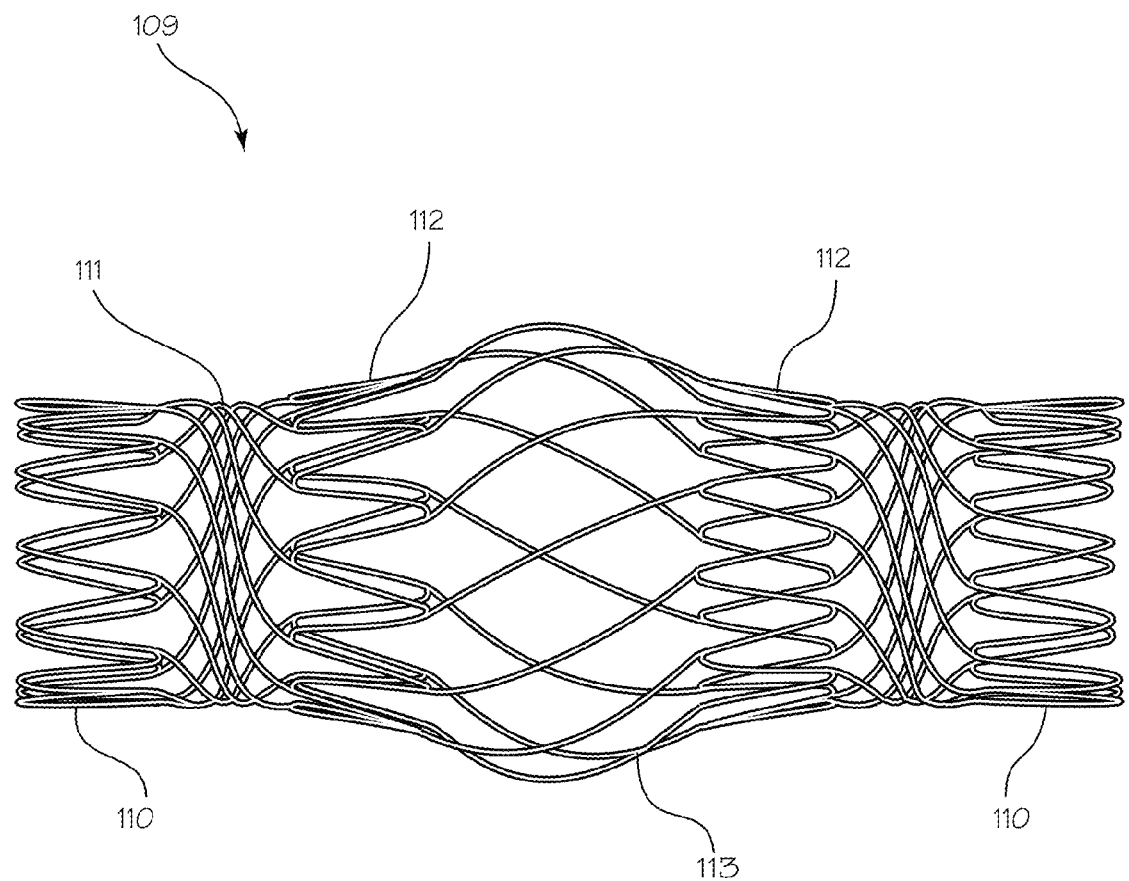
FIG. 21 illustrates a protuberant aneurysm bridging device fabricated from the flat pattern shown in FIG. 20 and formed into a cylindrical shape.

FIG. 21 illustrates a side view of a protuberant aneurysm bridging device 109 fabricated from the flat pattern 104. The device 109 comprises two end regions 110, one at each end. The device 109 further comprises a central region comprising two first intermediate sections 111 and two second intermediate sections 112, on both sides of the central spiral strut section 113. All sections and struts are preferably formed integrally, as is the case for most devices disclosed within this document. The number of repeat patterns in FIG. 21 is 16 resulting in a device 109 with a high metal to open space ratio relative to the devices fabricated from the flat pattern in FIG. 16. The first intermediate sections 111 and the central section 113 comprise more open space than the rest of the device 109.

Figure 22:
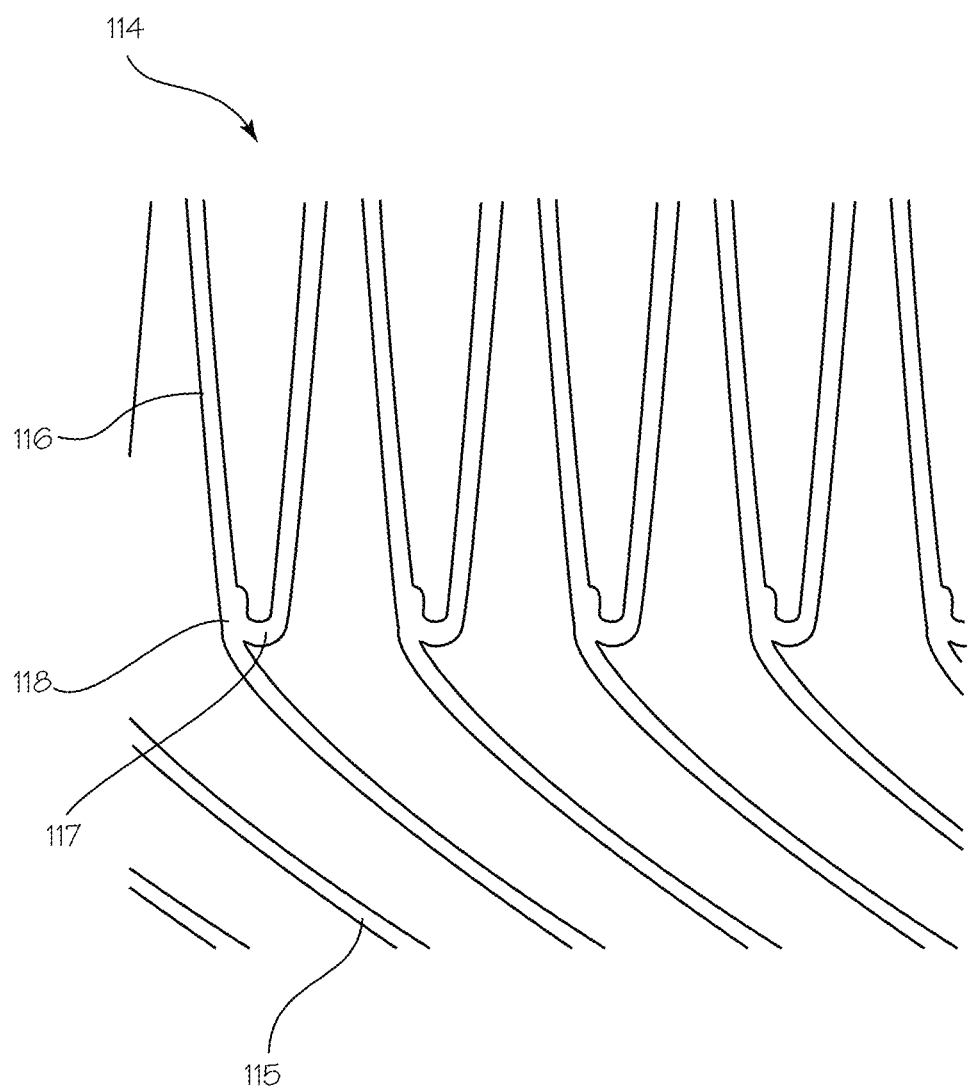
FIG. 22 illustrates a close-up of a protuberant aneurysm bridging device flat pattern such as that of FIG. 20 illustrating details of the bar geometry.

FIG. 22 illustrates a close-up of a protuberant aneurysm bridging device 114, which is similar to the device 109 of FIG. 21. The device 114 comprises the central region 115, the second intermediate region 116, the arcuate ends 117 of the second intermediate region 116, and the connector region 118. The connector region 118 is slightly thicker than the majority of the bar structure of the device 114. This increased thickness or bar width in the connector region 118 provides additional stiffness and strength in the connector region. The connector region 118 is affixed to the arcuate region 117 connecting the adjacent bars of the secondary intermediate region 116.

Figure 23:
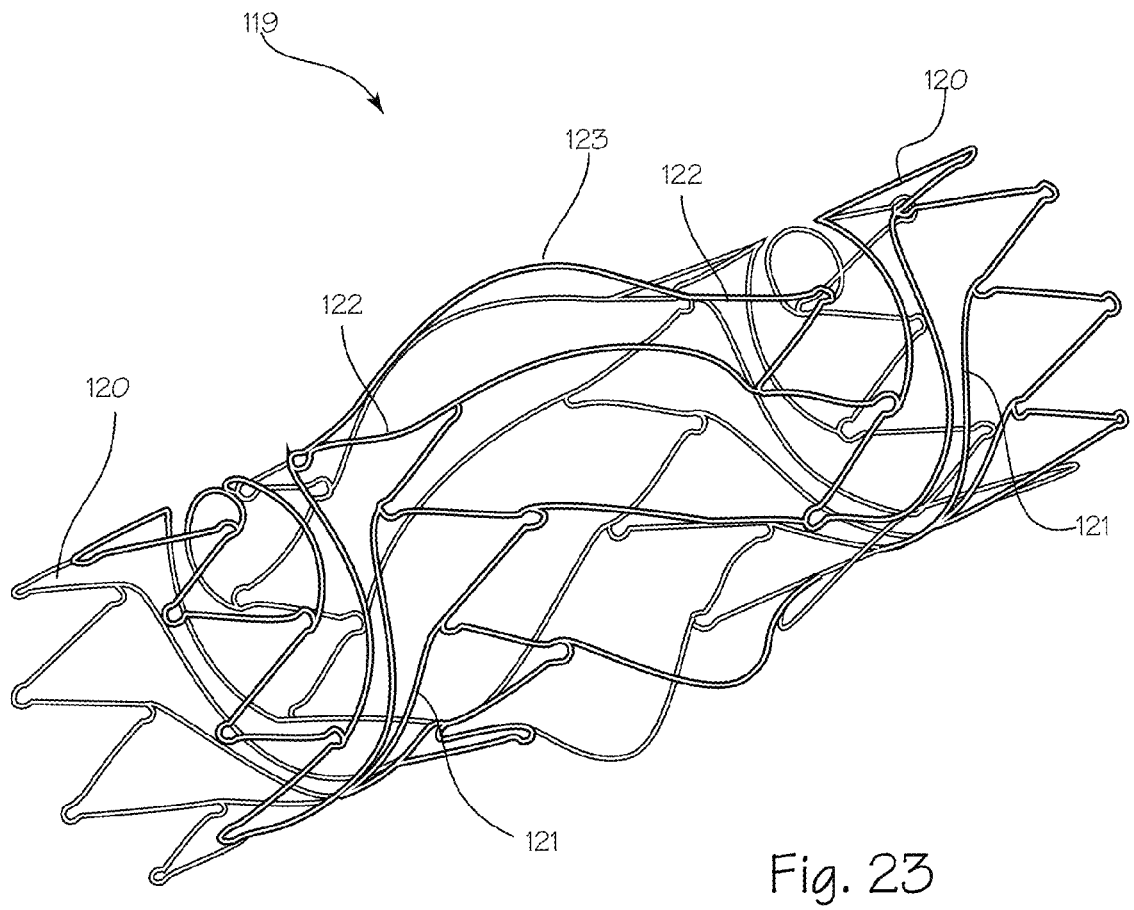
FIG. 23 illustrates an oblique view of a protuberant aneurysm bridging device formed into a cylindrical shape and constructed from a flat pattern such as that shown in FIG. 20.

FIG. 23 illustrates an oblique view of a protuberant aneurysm bridging device 119 having eight repeat patterns in the circumferential direction. The device 119 comprises the first and second end regions 120, and a central region comprising two first intermediate regions 121, two secondary intermediate regions 122, and a central spiral strut region 123. The protuberant aneurysm bridging device 119 has more open space ratio than devices having greater numbers of repeat patterns such as shown in FIGS. 17, 18, and FIG. 21. The secondary intermediate region 122 comprises relatively short strut lengths.

Figure 24:
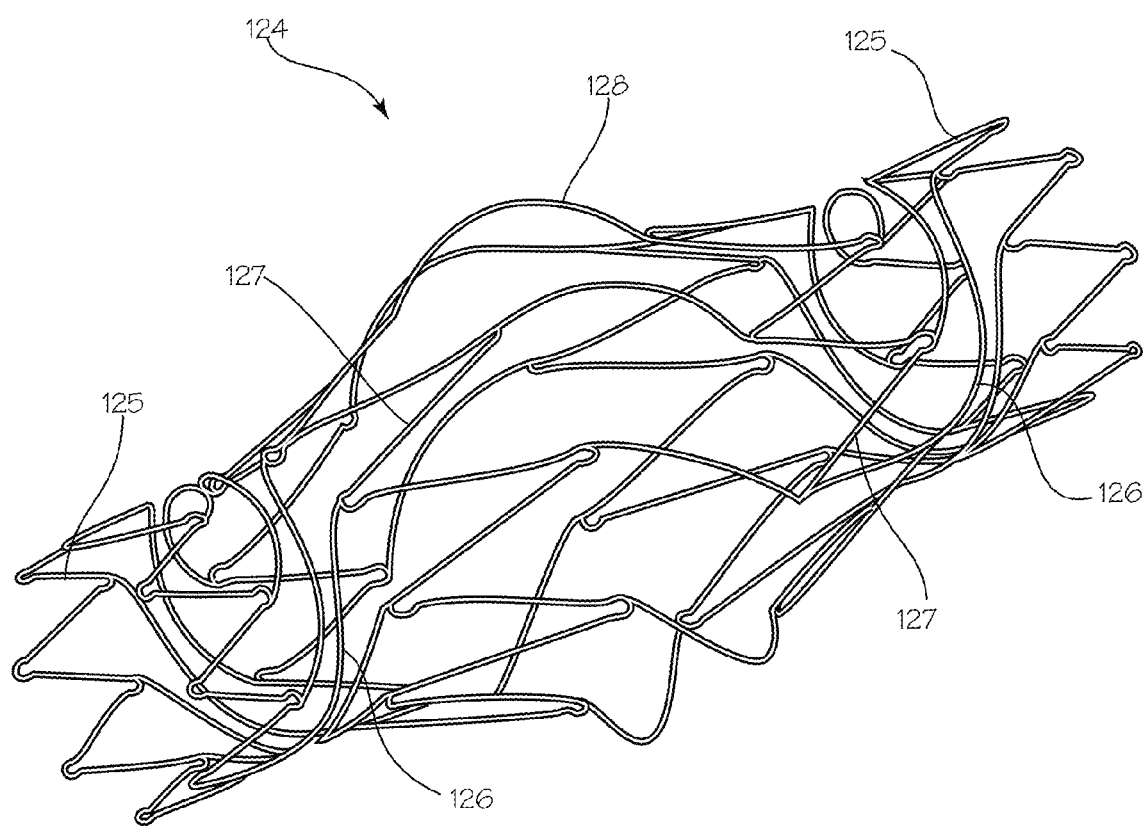
FIG. 24 illustrates an oblique view of a cylindrically formed protuberant aneurysm bridging device with less severe bending than that of the device in FIG. 23.

FIG. 24 illustrates a protuberant aneurysm bridging device 124 in oblique view comprising two end regions 125, two first intermediate regions 126 (with spiral struts), two secondary intermediate regions 127 (zigzag segments) and a central region 128. This protuberant aneurysm bridging device 124 is similar to the device 119 of FIG. 23 except that the bars in the secondary intermediate region 127 are longer than those in the secondary intermediate region 122 of FIG. 23. Both the device 124 and the device 119 comprise eight bars and eight spaces moving circumferentially in the central sections 123 and 128.

Figure 25A:
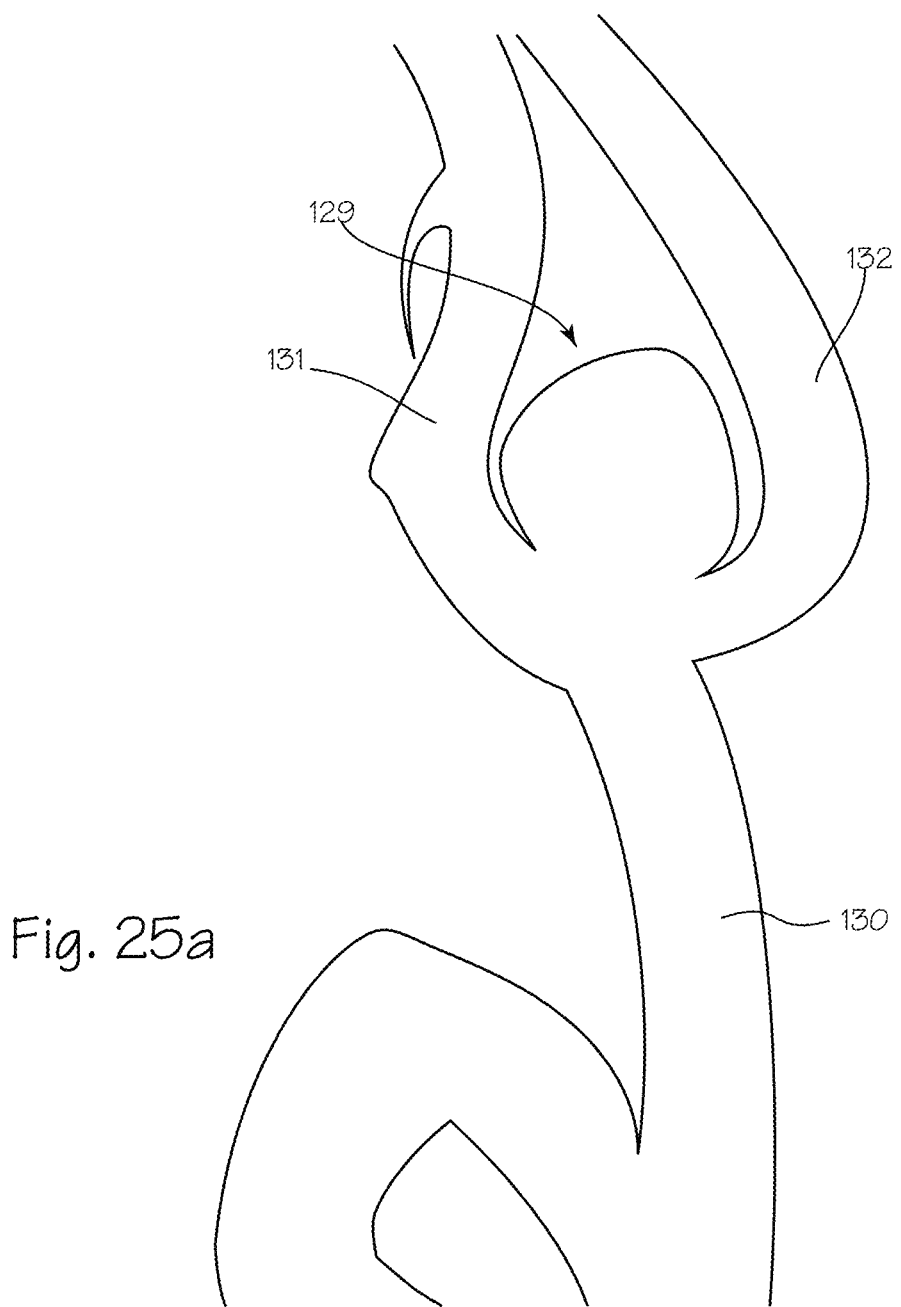
FIG. 25a illustrates a cerebrovascular aneurysm located at a vessel bifurcation.

FIG. 25a illustrates a cerebrovascular aneurysm 129 taken with fluoroscopy and dye injection wherein the aneurysm 129 is located at the junction of a bifurcation comprising an inflow artery 130, a first exit artery 131, and a second outflow artery 132.

Figure 25B:
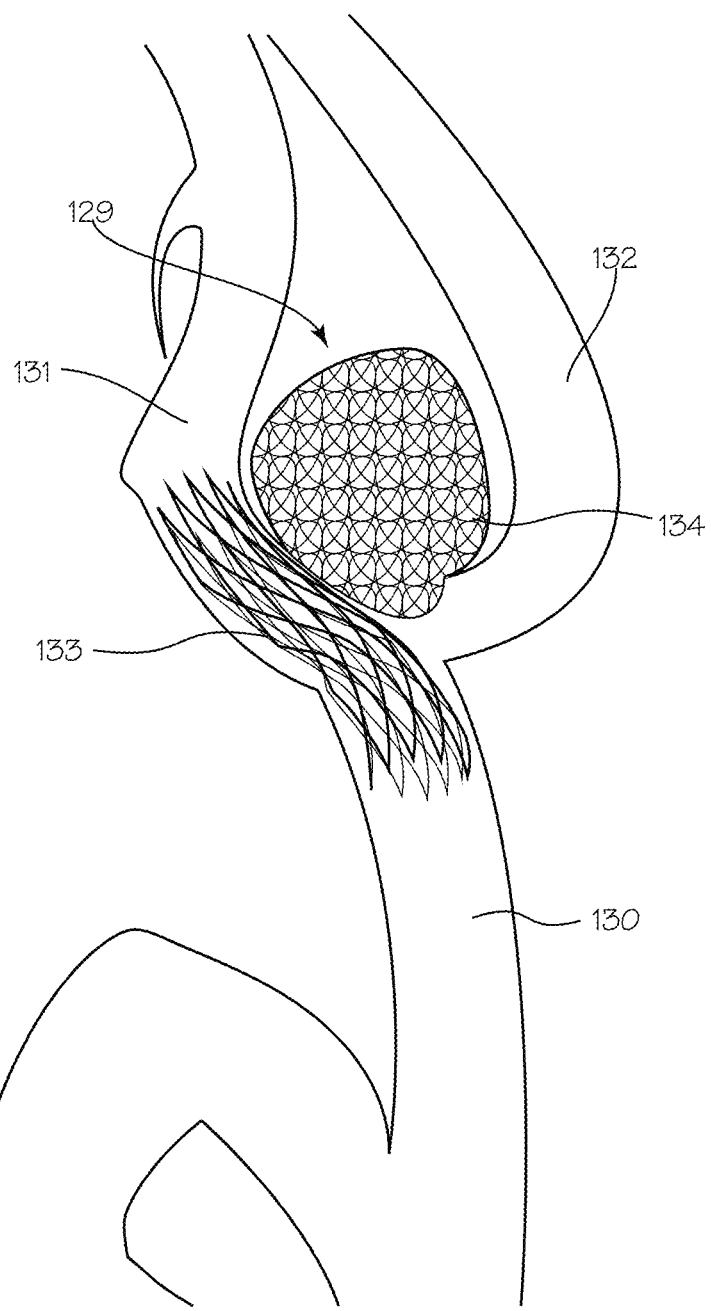
FIG. 25b illustrates a cerebrovascular aneurysm located at a vessel bifurcation with a commercially available cerebrovascular stent placed across the neck of the aneurysm.

FIG. 25b illustrates a cerebrovascular aneurysm 125 taken with fluoroscopy and dye injection wherein the aneurysm 129 is located at the junction of a bifurcation comprising an inflow artery 130, a first exit artery 131, and a second outflow artery 132. A simplified example of a commercially available cerebrovascular stent 133 is illustrated placed within the bifurcation such that the inlet to the device 133 is coaxial with the inlet artery 130 and the outlet of the device 133 is coaxial with the first outlet artery 131. An embolizing mass, such as platinum coils 134, is shown within the aneurysm 129. The stent 133 is shown placed across the entrance to, or the neck of, the aneurysm 129 allowing the coil mass to occlude the entrance to the secondary outlet artery 132.

Figure 25C:
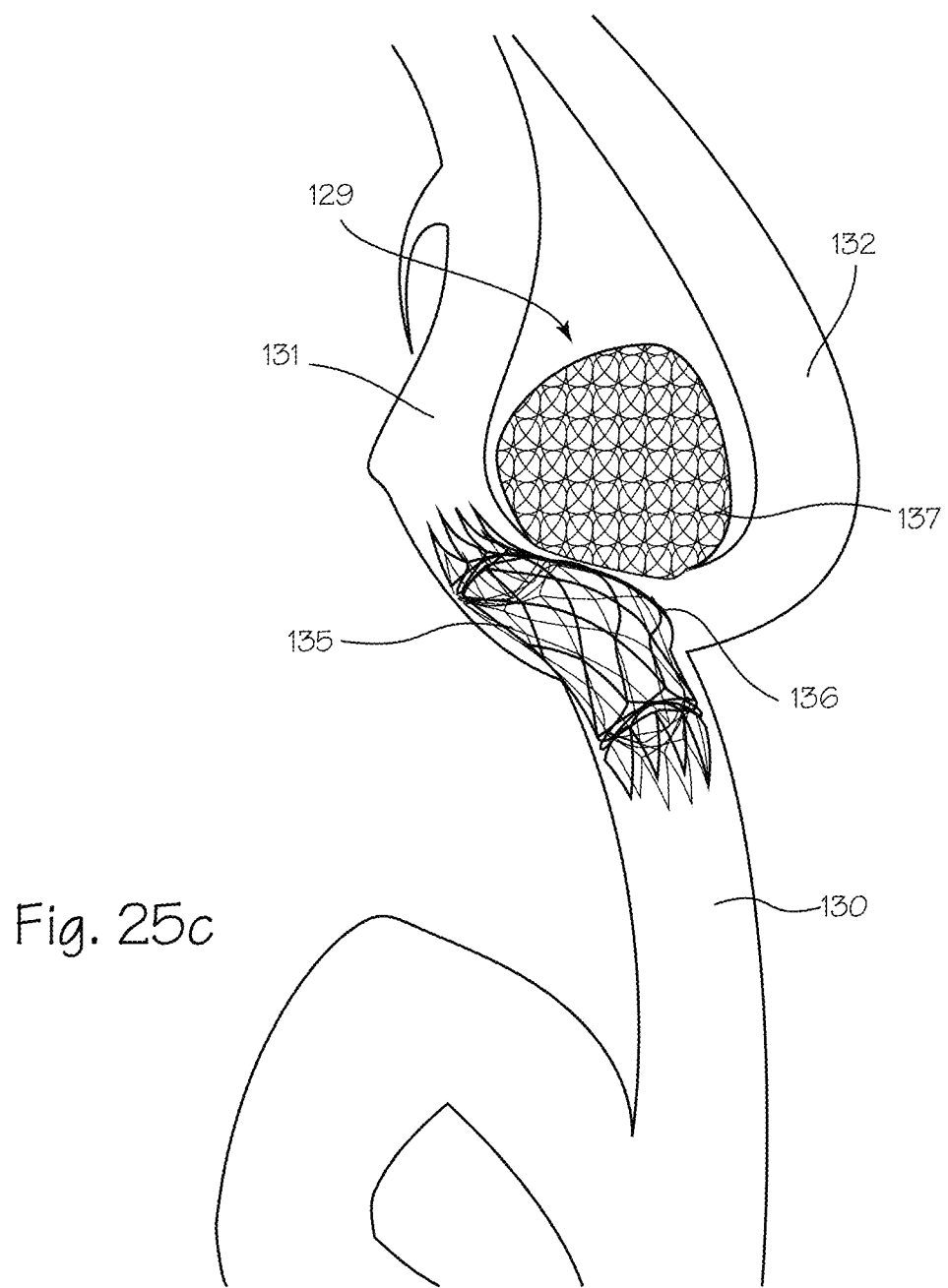
FIG. 25c illustrates a cerebrovascular aneurysm located at a vessel bifurcation with a protuberant aneurysm bridging device placed across and partially within the neck of the aneurysm.

FIG. 25c illustrates a cerebrovascular aneurysm 129 taken with fluoroscopy and dye injection wherein the aneurysm 129 is located at the junction of a bifurcation comprising an inflow artery 130, a first exit artery 131, and a second outflow artery 132. A simplified example of a protuberant aneurysm bridging device 135 is illustrated placed within the bifurcation such that the inlet to the device 135 is coaxial with the inlet artery 130 and the outlet of the device 135 is coaxial with the first outlet artery 131. An embolizing platinum coil mass is shown within the aneurysm 129. The protuberant aneurysm bridging device 135 is shown placed across the entrance to, or the neck of, the aneurysm 129 and protruding into the aneurysm neck holding, via the central bulge 136 of the device and supporting the platinum coil mass 137 to allow flow into the entrance to the secondary outlet artery 132. The bars of the device 135 are widely spaced in the region of the secondary outlet artery 138 inlet as well as in the region of the aneurysm 129 neck such that blood is free to flow through these widely spaced device bars while providing some holding power to the embolizing coil mass 137.

Figure 26A:
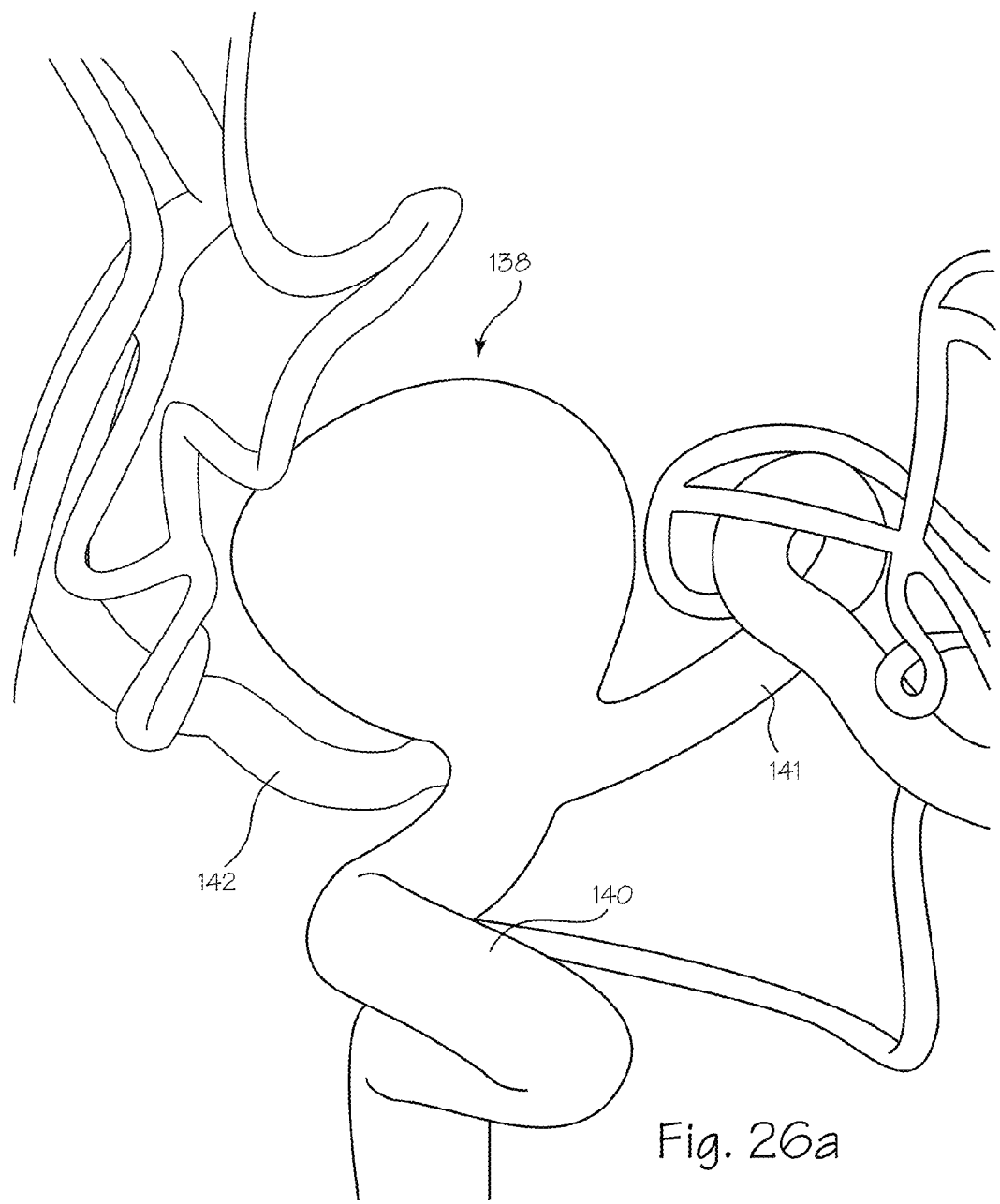
FIG. 26a illustrates a giant cerebrovascular aneurysm located at a vessel bifurcation.

FIG. 26a illustrates a giant bifurcate cerebrovascular aneurysm 139 at a bifurcation with an entrance vessel 140 to the bifurcation, a first outflow vessel 141 and a second outlet vessel 142.

Figure 26B:
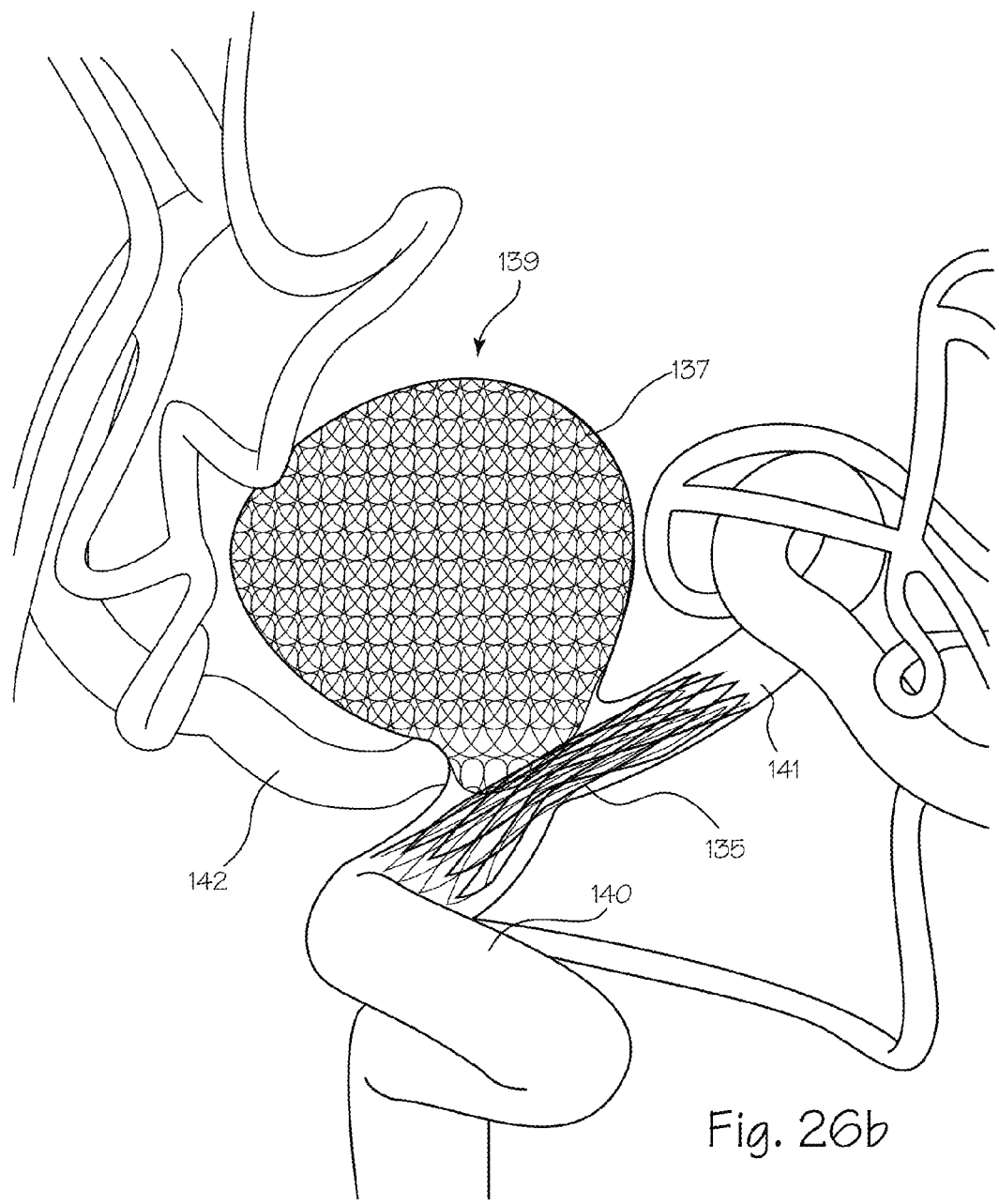
FIG. 26b illustrates a giant cerebrovascular aneurysm with illustrates a cerebrovascular aneurysm located at a vessel bifurcation with a commercially available cerebrovascular stent placed across the neck of the aneurysm.

FIG. 26b illustrates a giant bifurcate cerebrovascular aneurysm 139 taken with fluoroscopy and dye injection wherein the aneurysm 139 is located at the junction of a bifurcation comprising an inflow artery 140, a first exit artery 141, and a second outflow artery 142. A simplified example of a commercially available cerebrovascular stent 133 is illustrated placed within the bifurcation such that the inlet to the device 133 is coaxial with the inlet artery 140 and the outlet of the device 133 is coaxial with the first outlet artery 141. An embolizing mass, such as platinum coils 134, is shown within the aneurysm 139. The stent 133 is shown placed across the entrance to, or the neck of, the aneurysm 139 allowing the coil mass to occlude the entrance to the secondary outlet artery 142.

Figure 26C:
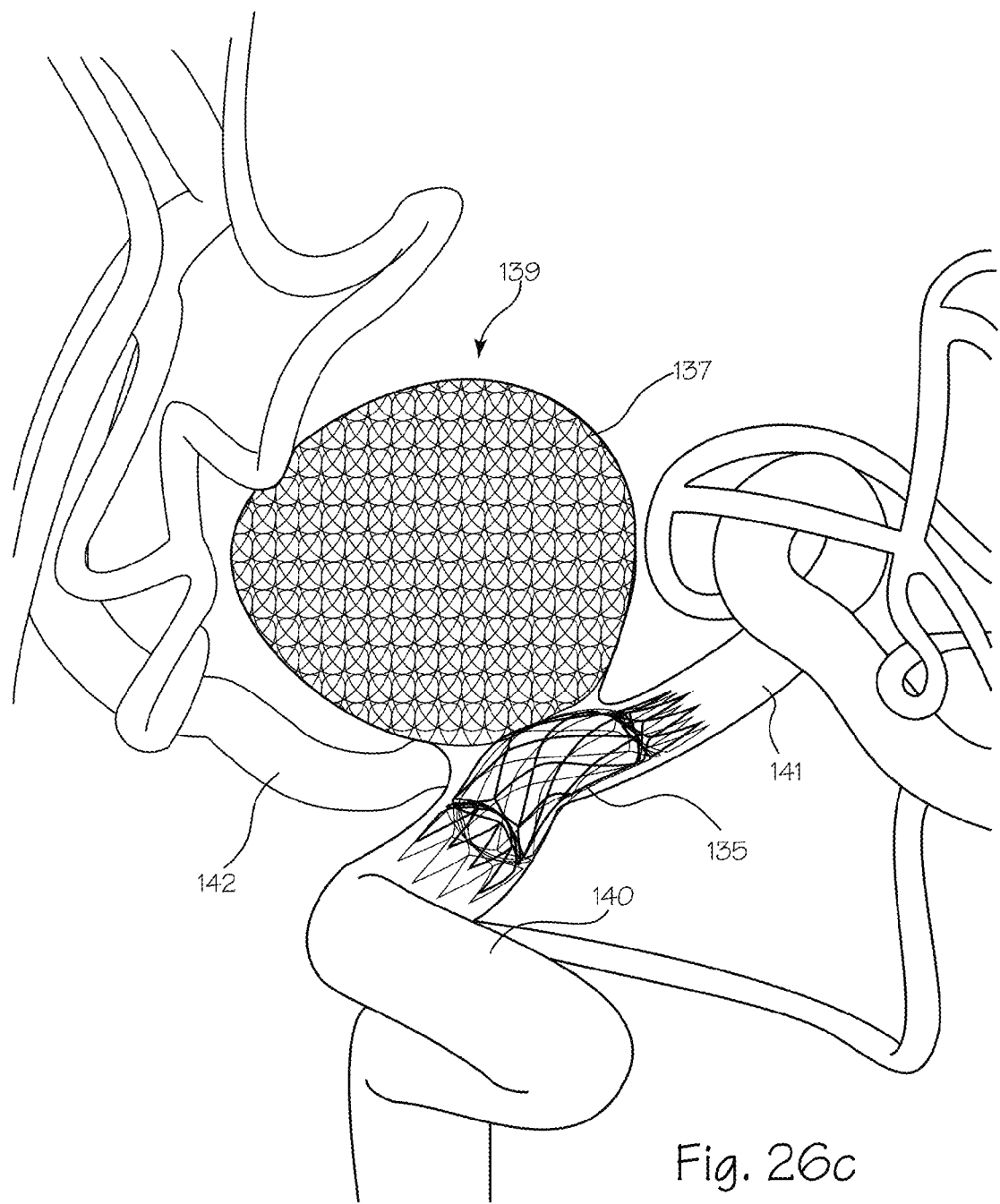
FIG. 26c illustrates a giant cerebrovascular aneurysm with a stylized device slightly herniating into the aneurysm neck and the second of two bifurcation outflow vessels.

FIG. 26c illustrates a giant bifurcate cerebrovascular aneurysm 139 taken with fluoroscopy and dye injection wherein the aneurysm 139 is located at the junction of a bifurcation comprising an inflow artery 140, a first exit artery 141, and a second outflow artery 142. A simplified example of a protuberant aneurysm bridging device 135 is illustrated placed within the bifurcation such that the inlet to the device 135 is coaxial with the inlet artery 140 and the outlet of the device 135 is coaxial with the first outlet artery 141. An embolizing platinum coil mass is shown within the aneurysm 139. The protuberant aneurysm bridging device 135 is shown placed across the entrance to, or the neck of, the aneurysm 139 and protruding into the aneurysm neck holding, via the central bulge of the device 135 and supporting the platinum coil mass 134 to allow flow into the entrance to the secondary outlet artery 142. The bars of the device 135 are widely spaced in the region of the secondary outlet artery 142 inlet as well as in the region of the aneurysm 139 neck such that blood is free to flow through these widely spaced device bars while providing some holding power to the embolizing coil mass 134.

Figure 27A:
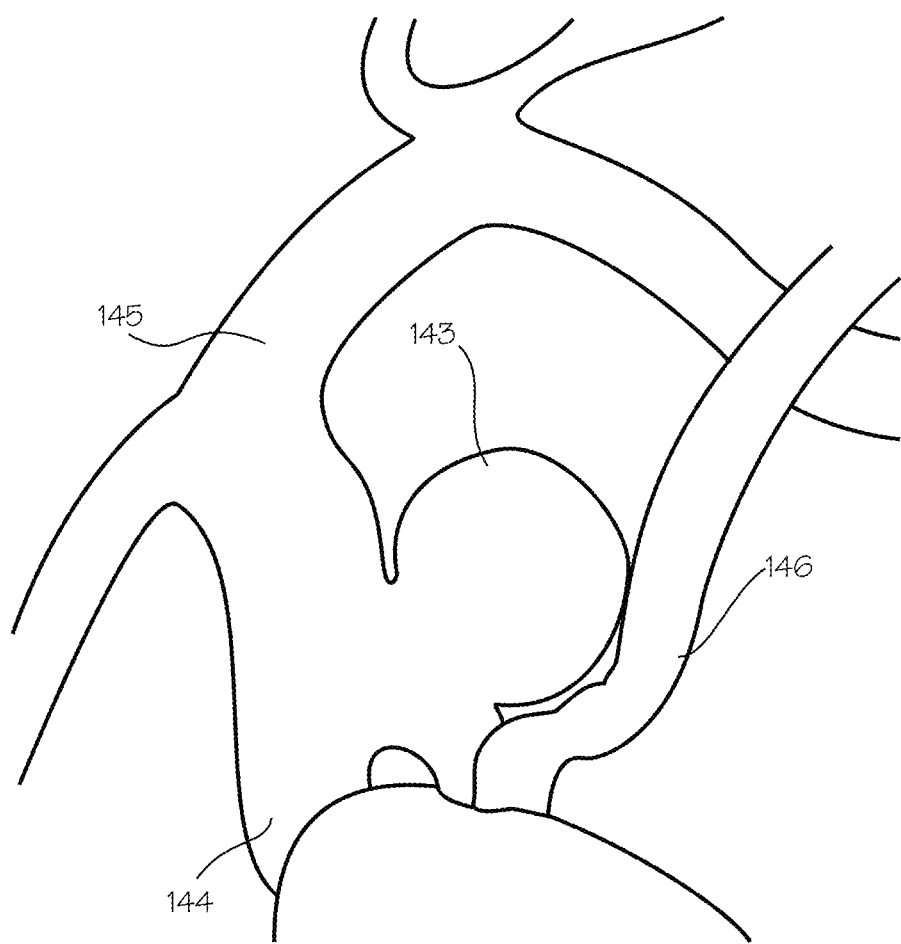
FIG. 27a illustrates a cerebrovascular aneurysm located at a vessel bifurcation.

FIG. 27a illustrates a cerebrovascular aneurysm 143 taken with fluoroscopy and dye injection wherein the aneurysm is located at the junction of a bifurcation comprising an inflow artery 144, a first exit artery 145, and a second outflow artery 146.

Figure 27B:
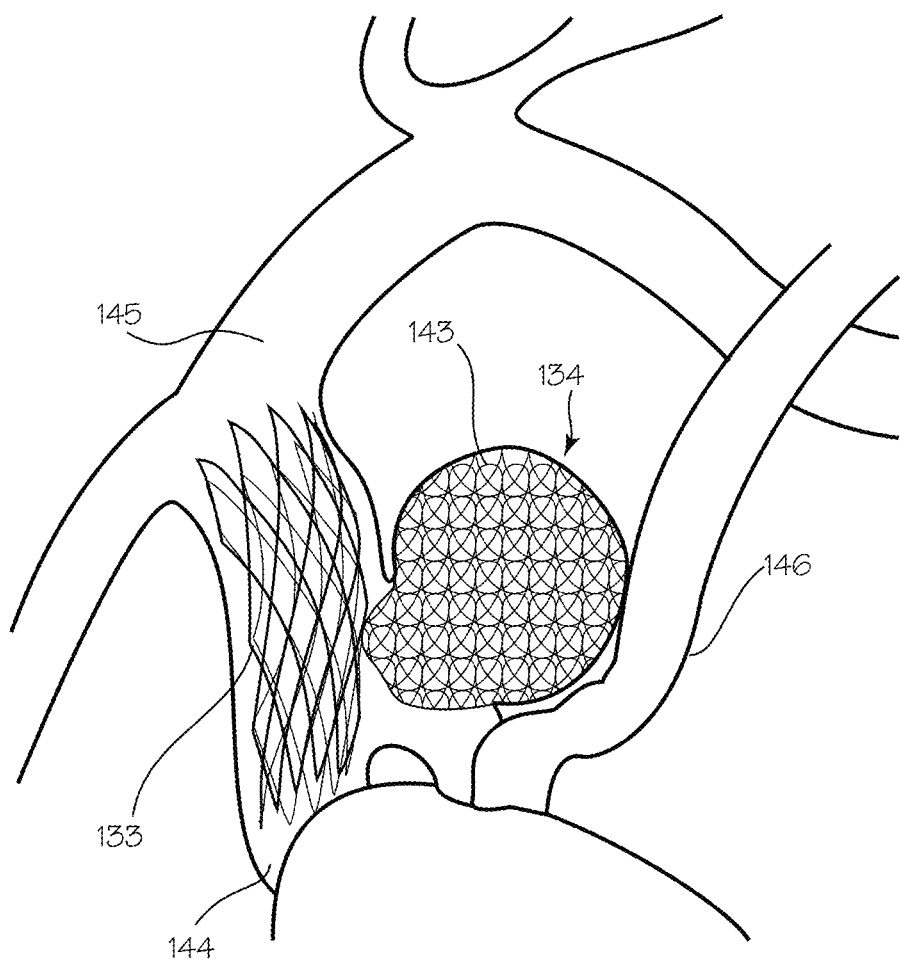
FIG. 27b illustrates a giant cerebrovascular aneurysm located at a vessel bifurcation with a commercially available cerebrovascular stent placed across the neck of the aneurysm.

FIG. 27b illustrates a cerebrovascular aneurysm 143 taken with fluoroscopy and dye injection wherein the aneurysm 143 is located at the junction of a bifurcation comprising an inflow artery 144, a first exit artery 145, and a second outflow artery 146. A simplified example of a commercially available cerebrovascular stent 133 is illustrated placed within the bifurcation such that the inlet to the device 133 is coaxial with the inlet artery 144 and the outlet of the device 133 is coaxial with the first outlet artery 145. An embolizing mass, such as platinum coils 134, is shown within the aneurysm 143. The stent 133 is shown placed across the entrance to, or the neck of, the aneurysm 143 allowing the coil mass to occlude the entrance to the secondary outlet artery 146.

Figure 27C:
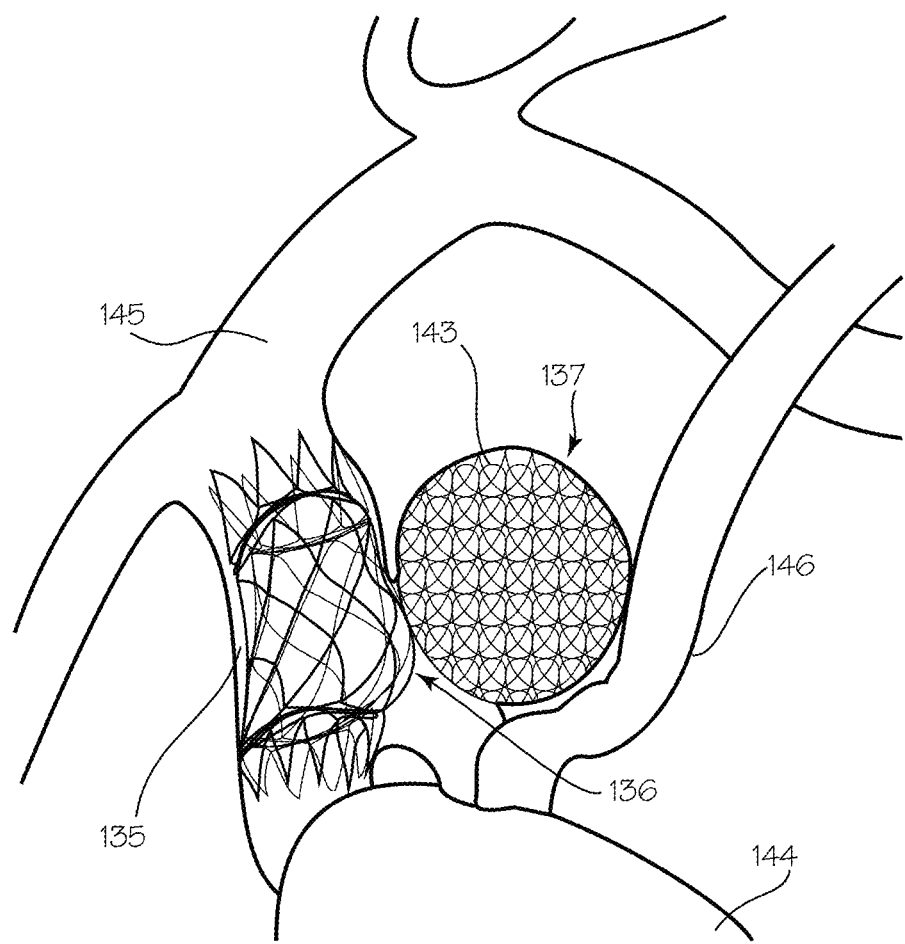
FIG. 27c illustrates a cerebrovascular aneurysm with a stylized device placed across the aneurysm neck and the bifurcation inflow vessel.

FIG. 27c illustrates a cerebrovascular aneurysm 143 taken with fluoroscopy and dye injection wherein the aneurysm 143 is located at the junction of a bifurcation comprising an inflow artery 144, a first exit artery 145, and a second outflow artery 146. A simplified example of a protuberant aneurysm bridging device 135 is illustrated placed within the bifurcation such that the inlet to the device 135 is coaxial with the inlet artery 144 and the outlet of the device 135 is coaxial with the first outlet artery 145. An embolizing platinum coil mass is shown within the aneurysm 143. The protuberant aneurysm bridging device 135 is shown placed across the entrance to, or the neck of, the aneurysm 143 and protruding into the aneurysm neck, and holding, via the central bulge of the device 135, and supporting the platinum coil mass 134 to allow flow into the entrance to the secondary outlet artery 146. The bars of the device 135 are widely spaced in the region of the secondary outlet artery 146 inlet as well as in the region of the aneurysm 143 neck such that blood is free to flow through these widely spaced device bars while providing some holding power to the embolizing coil mass 134.

Figure 28A:
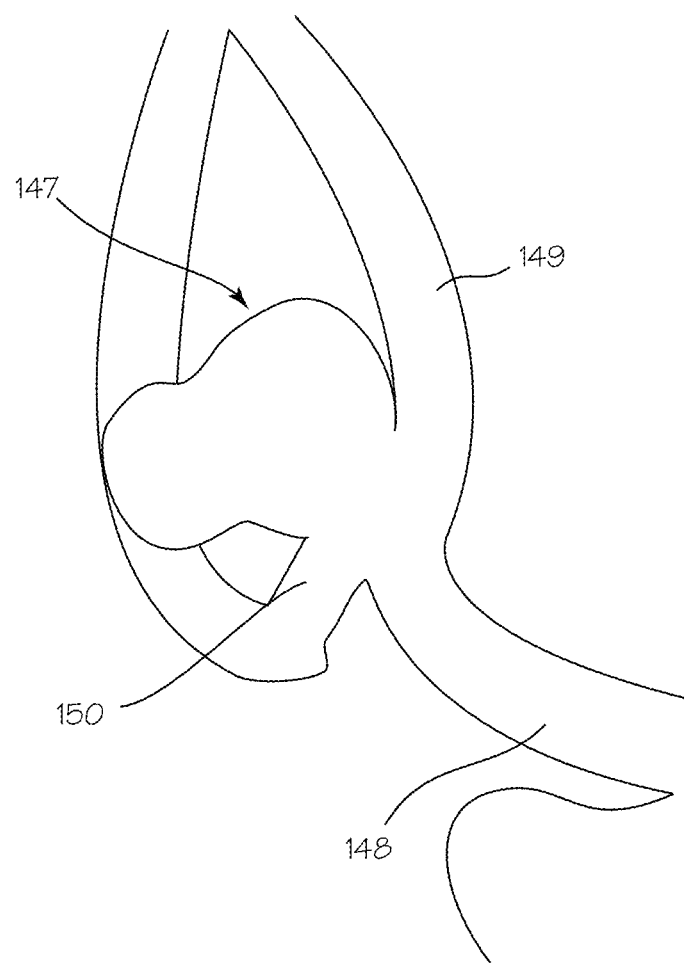
FIG. 28a illustrates a small cerebrovascular aneurysm at a trifurcation with a stylized device slightly herniating into the aneurysm neck and two of the trifurcation exit vessels.

FIG. 28*a* illustrates a cerebrovascular aneurysm 147 taken with fluoroscopy and dye injection wherein the aneurysm 147 is located at the junction of a bifurcation comprising an inflow artery 148, a first exit artery 149, and a second outflow artery 150.

Figure 28B:
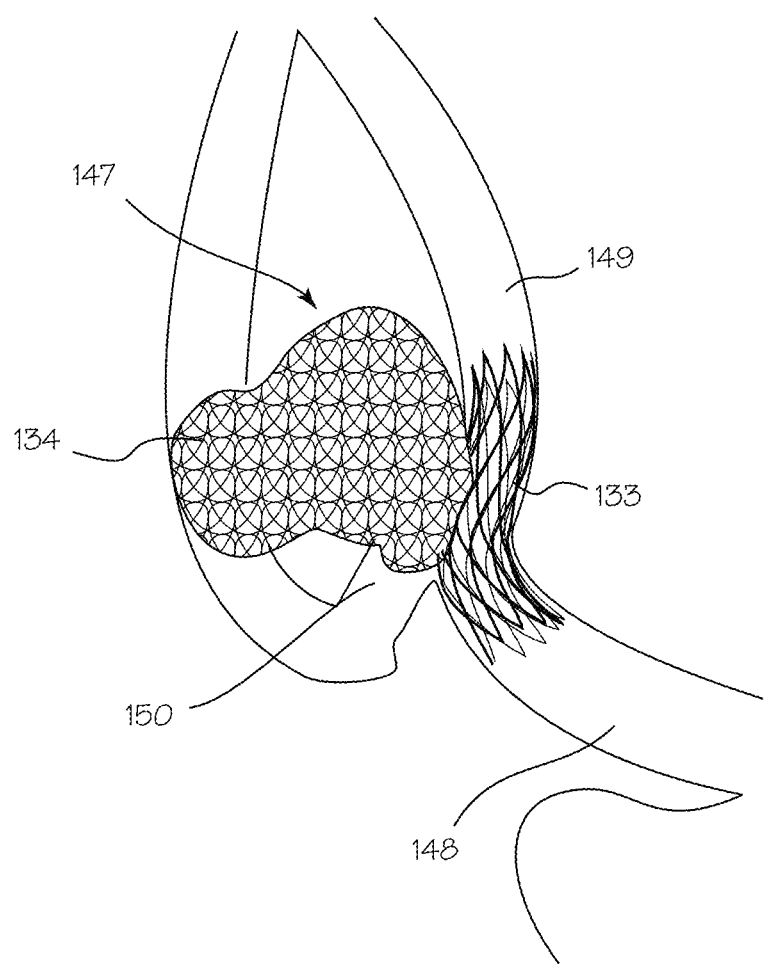
FIG. 28b illustrates a cerebrovascular aneurysm located at a vessel bifurcation with a commercially available cerebrovascular stent placed across the neck of the aneurysm.

FIG. 28*b* illustrates a cerebrovascular aneurysm 147 taken with fluoroscopy and dye injection wherein the aneurysm 147 is located at the junction of a bifurcation comprising an inflow artery 148, a first exit artery 149, and a second outflow artery 150. A simplified example of a commercially available cerebrovascular stent 133 is illustrated placed within the bifurcation such that the inlet to the device 133 is coaxial with the inlet artery 148 and the outlet of the device 133 is coaxial with the first outlet artery 149. An embolizing mass, such as platinum coils 134, is shown within the aneurysm 147. The stent 133 is shown placed across the entrance to, or the neck of, the aneurysm 147 allowing the coil mass to occlude the entrance to the secondary outlet artery 150.

Figure 28C:
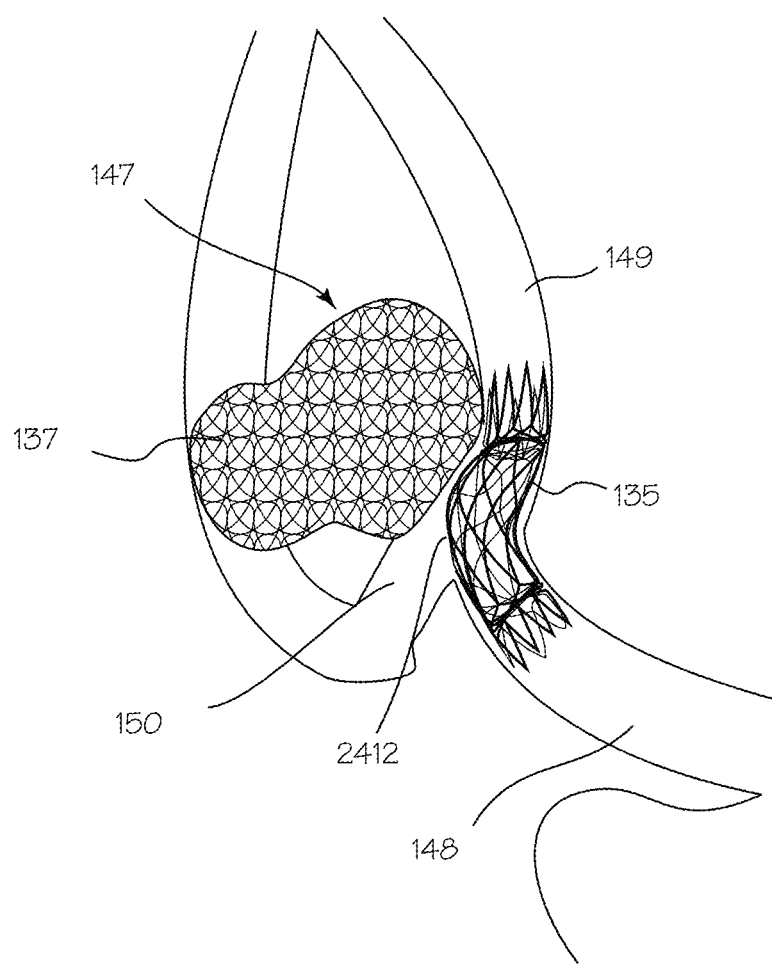
FIG. 28c illustrates a cerebrovascular aneurysm with a stylized device placed across the aneurysm neck and the bifurcation inflow vessel.

FIG. 28*c* illustrates a cerebrovascular aneurysm 147 taken with fluoroscopy and dye injection wherein the aneurysm 147 is located at the junction of a bifurcation comprising an inflow artery 148, a first exit artery 149, and a second outflow artery 150. A simplified example of a protuberant aneurysm bridging device 135 is illustrated placed within the bifurcation such that the inlet to the device 135 is coaxial with the inlet artery 148 and the outlet of the device 135 is coaxial with the first outlet artery 149. An embolizing platinum coil mass is shown within the aneurysm 147. The protuberant aneurysm bridging device 135 is shown placed across the entrance to, or the neck of, the aneurysm 147 and protruding into the aneurysm neck, holding, via the central bulge of the device 135, and supporting the platinum coil mass 134 to allow flow into the entrance to the secondary outlet artery 150. The bars of the device 135 are widely spaced in the region of the secondary outlet artery 150 inlet as well as in the region of the aneurysm 147 neck such that blood is free to flow through these widely spaced device bars while providing some holding power to the embolizing coil mass 134.

Each of the protuberant aneurysm bridging device embodiments and be controlled with the various methods used for devices and other devices made of nitinol. Nitinol is preferred because its biocompatibility is well proven, and it is available in numerous compositions with well-controlled, predictable transition temperatures. Other shape memory or pseudoelastic materials can also be used, and normally elastic stainless steel, cobalt nickel alloys, and plastics may be used. The nitinol used for the device may be used in its shape memory formulation, with a transition temperature just above body temperature, in which case the device may be returned to its memorized shape upon the injection of warm water (just above body temperature). Alternatively, the nitinol used for the device may be used in its pseudoelastic formulations, in which the nitinol is superelastic (also called pseudoelastic) at body temperature, in which case the device will automatically revert to its memorized shape when inside the body. The superelastic device can be deformed to fit within the delivery catheter so that it can be inserted into the body, and it reverts to the memorized shape, utilizing elasticity, phase changes, or both, when released from the catheter in the blood stream.

Common among the embodiments of the aneurysm occluding devices is the desire that the occluding structure enhance formation of thrombus within the aneurysm. To enhance this function, the occluding structure may be coated with known thrombogenic materials such as platinum. The struts which remain outside the aneurysm sac and within the blood stream preferably remain uncoated with such a thrombogenic coating, and are preferably coated with an anti-thrombogenic coating such as heparin, tin, or other such coatings as previously disclosed in the medical device art. Thus the occluding device can comprise segments of varying thrombo-active coatings, depending on the desired characteristic of each segment. The devices can also be coated with materials such as tantalum, gold and platinum in order to enhance the visibility of the devices under fluoroscopy. The devices can be clearly visualized under intravascular ultrasound which can be used to aid in deployment and proper placement. While the devices will provide for the primary treatment of aneurysms, they may also be used in conjunction with embolic materials such as, but not limited to, baskets, embolic coils, hardenable polymers, and the like in order to hold these foreign materials within the aneurysm and prevent their migration from the aneurysm into the blood stream.

Certain aspects of the inventions include methods of implantation of the protuberant aneurysm bridging device. In some embodiments of the method, the devices is loaded into a delivery microcatheter. Under anesthesia and using standard hospital aseptic technique, a Seldinger technique can be used to obtain percutaneous access to the femoral artery and an optional introducer sheath can be retained within the arterial access site to aid in device insertion and removal. A guide catheter can be routed through the femoral access site to the cerebrovasculature, or as close as possible, with the aid of a guidewire. The guidewire can be removed and the device delivery microcatheter can be introduced through the guide catheter and advanced into the Basilar artery, the circle of Willis, or other location. The device delivery microcatheter can be advanced under fluoroscopic guidance, single or bi-planar, to the target region. The distal end of the device delivery microcatheter can be advanced into the first outlet vessel of a bifurcation. The proximal end of the device delivery microcatheter can be retained well within the inlet vessel to the bifurcation. The radiopaque markers can be aligned at this time to ensure the device deploys with the open mesh directed toward the entrance to the second exit vessel. The protuberant aneurysm bridging device can be expanded using an angioplasty type balloon or using internal recovery such as spring biasing, shape memory transformation, or the like. The position of the protuberant aneurysm bridging device can be confirmed using fluoroscopy, IVUS, MRI, or the like. Further expansion of the protuberant aneurysm bridging device can be performed, if necessary, prior to final detachment of the device from the delivery catheter and removal of the device delivery catheter from the patient. Following placement of the device, a microcatheter can be used to delivery embolic devices into the aneurysm through the open walls of the central region of the device. When the procedure is completed and fully interrogated to ensure correct treatment (e.g. no embolic coils protruding into the parent vessel), the embolic device delivery devices can be removed from the patient.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of treating a wide-necked aneurysm at a bifurcation of a parent artery into a first and second branch artery, said wide-necked aneurysm characterized by a neck opening into the bifurcation, said method comprising:
   providing a bridging device in a first catheter and delivering said bridging device to the neck of the aneurysm;
   said bridging device comprising a wire frame structure characterized by a distal region, a proximal region, and a bridging region disposed between the distal region and the proximal region, said bridging device being self-expandable from a small diameter configuration and a large diameter configuration;
   placing a distal segment of a first catheter across the neck of the aneurysm;
   deploying the distal region of the bridging device from the distal segment of the first catheter while maintaining the bridging device in secure connection to a delivery wire, such that the distal regions expands to engage the wall of the first branch artery thereby fixing the distal region within the first branch artery;
   adjusting the position of the bridging device, so that a proximal edge of the distal region of substantially cylindrical cross-section is aligned with the junction of the aneurysm neck and the first branch artery; and thereafter
   deploying a bridging portion of the bridging device from the distal segment of the catheter so that the bridging portion is disposed adjacent the aneurysm neck, spanning the aneurysm neck;
   pushing the proximal region of the bridging device to longitudinally compress the bridging region and force the bridging region to assume a radially expanded configuration proximate the aneurysm neck;
   removing the proximal region of substantially cylindrical cross-section from the distal segment of the catheter so that the proximal region is disposed within the parent artery;
   delivering an occlusive device or substance from a second catheter into the aneurysm sac; and
   releasing the bridging device from the first catheter.

2. The method of claim 1 further comprising the step of:
   detaching the bridging device from the first catheter and removing the first catheter from the bifurcation, leaving the bridging device within the bifurcation, spanning the neck of the aneurysm.

3. The method of claim 1 further comprising the steps of:
   withdrawing the bridging device into the distal segment of the first catheter and removing the bridging device from the bifurcation after delivering the occlusive device or substance.

4. A method of treating a wide-necked aneurysm at a bifurcation of a parent artery into a first and second branch artery, said wide-necked aneurysm characterized by a neck opening into the bifurcation, said method comprising:
   providing a bridging device in a first catheter and delivering said bridging device to the neck of the aneurysm;
   said bridging device comprising a wire frame structure characterized by a distal region, a proximal region, and a bridging region disposed between the distal region and the proximal region, said bridging device being self-expandable from a small diameter configuration and a large diameter configuration;
   placing the distal region of first catheter across the neck of the aneurysm;
   deploying the distal region of the bridging device from the distal segment of the first catheter while maintaining the bridging device in secure connection to a delivery wire, such that the distal regions expands to engage the wall of the first branch artery thereby fixing the distal region within the first branch artery;
   adjusting the position of the bridging device, so that a proximal edge of the distal region of substantially cylindrical cross-section is aligned with the junction of the aneurysm neck and the first branch artery; and thereafter
   deploying the bridging region of the bridging device from the distal segment of the catheter so that the bridging region is disposed adjacent the aneurysm neck, spanning the aneurysm neck;
   pushing the proximal region of the bridging device to longitudinally compress the bridging portion and force the bridging portion to assume a radially expanded configuration proximate the aneurysm neck; and thereafter
   removing the proximal region of substantially cylindrical cross-section from the distal segment of the catheter so that the proximal segment is disposed within the parent artery;
   delivering an occlusive device or substance from a second catheter into the aneurysm sac; and
   releasing the bridging device from the first catheter.

5. The method of claim 4 further comprising the step of:
   detaching the bridging device from the first catheter and removing the first catheter from the bifurcation, leaving the bridging device within the bifurcation, spanning the neck of the aneurysm.

6. The method of claim 4 further comprising the steps of withdrawing the bridging device into the distal segment of the first catheter and removing the bridging device from the bifurcation after delivering the occlusive device or substance.

* * * * *